United States Patent
Suzuki et al.

(10) Patent No.: US 11,103,124 B2
(45) Date of Patent: Aug. 31, 2021

(54) POSITION DETECTION APPARATUS, POSITION DETECTION SYSTEM, AND POSITION DETECTION METHOD

(71) Applicant: OLYMPUS CORPORATION, Tokyo (JP)

(72) Inventors: Yusuke Suzuki, Hino (JP); Atsushi Chiba, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 60 days.

(21) Appl. No.: 16/537,734

(22) Filed: Aug. 12, 2019

(65) Prior Publication Data

US 2019/0357752 A1 Nov. 28, 2019

Related U.S. Application Data

(63) Continuation of application No. PCT/JP2017/036043, filed on Oct. 3, 2017.

(30) Foreign Application Priority Data

Mar. 16, 2017 (JP) .............................. JP2017-051500

(51) Int. Cl.
*A61B 1/00* (2006.01)
*H04B 17/318* (2015.01)
(Continued)

(52) U.S. Cl.
CPC ........ *A61B 1/00016* (2013.01); *A61B 1/0002* (2013.01); *A61B 1/00006* (2013.01);
(Continued)

(58) Field of Classification Search
CPC combination set(s) only.
See application file for complete search history.

(56) References Cited

U.S. PATENT DOCUMENTS 6,236,335 B1* 5/2001 Goodwin, III ........ G01S 5/0252
340/8.1
9,131,842 B2* 9/2015 Old ...................... A61B 5/0002
(Continued)

FOREIGN PATENT DOCUMENTS

JP 2003-019111 A 1/2003
JP 2011188413 A * 9/2011
(Continued)

OTHER PUBLICATIONS

Miyazawa, Akira, JP-2011188413-A Translation, Sep. 2011 (Year: 2011).*

(Continued)

*Primary Examiner* — Lewis G West
(74) *Attorney, Agent, or Firm* — Scully, Scott, Murphy & Presser, P.C.

(57) ABSTRACT

A position detection apparatus includes: a first antenna attached to a predetermined position of a subject and configured to receive a wireless signal transmitted from a medical apparatus inserted into the subject; a second antenna attached to the subject at a different position relative to the first antenna and configured to receive the wireless signal; and a processor comprising hardware. The processor is configured to: calculate a first received strength of the wireless signal received by the first antenna and a second received strength of the wireless signal received by the second antenna; calculate an attachment position of the second antenna based on the first and the second received strengths; and calculate a position of the medical apparatus based on: the first and the second received strengths; the calculated position of the first antenna; and the calculated position of the second antenna.

9 Claims, 14 Drawing Sheets

(51) Int. Cl.
    *A61B 1/04* (2006.01)
    *G01S 5/14* (2006.01)
(52) U.S. Cl.
    CPC ...... *A61B 1/00032* (2013.01); *A61B 1/00043* (2013.01); *A61B 1/041* (2013.01); *G01S 5/14* (2013.01); *H04B 17/318* (2015.01)

(56) References Cited

U.S. PATENT DOCUMENTS

| | | | | |
|---|---|---|---|---|
| 10,346,657 | B1* | 7/2019 | White | H05B 47/19 |
| 2002/0050943 | A1* | 5/2002 | Toda | G01S 19/55 |
| | | | | 342/357.38 |
| 2003/0073935 | A1* | 4/2003 | Segawa | A61B 1/00016 |
| | | | | 600/593 |
| 2006/0252987 | A1* | 11/2006 | Hasegawa | A61B 1/00009 |
| | | | | 600/101 |
| 2007/0241975 | A1* | 10/2007 | Kimoto | A61B 1/00016 |
| | | | | 343/718 |
| 2007/0270628 | A1* | 11/2007 | Kawano | A61B 1/00158 |
| | | | | 600/12 |
| 2009/0002177 | A1* | 1/2009 | Kimoto | A61B 1/00055 |
| | | | | 340/573.1 |
| 2009/0043164 | A1* | 2/2009 | Hasegawa | A61B 1/00002 |
| | | | | 600/118 |
| 2009/0046821 | A1* | 2/2009 | Shigemori | A61B 1/041 |
| | | | | 375/371 |
| 2009/0259096 | A1* | 10/2009 | Shigemori | A61B 1/00055 |
| | | | | 600/109 |
| 2009/0312604 | A1* | 12/2009 | Kimoto | H04B 17/23 |
| | | | | 600/118 |
| 2011/0256895 | A1* | 10/2011 | Palin | H04M 1/7253 |
| | | | | 455/509 |
| 2011/0282165 | A1* | 11/2011 | Kawano | A61B 1/041 |
| | | | | 600/302 |
| 2011/0294519 | A1* | 12/2011 | Laine | G01S 5/0205 |
| | | | | 455/456.1 |
| 2012/0003951 | A1* | 1/2012 | Kawaguchi | G06K 7/0008 |
| | | | | 455/337 |
| 2012/0007973 | A1* | 1/2012 | Tsutsumi | A61B 1/00016 |
| | | | | 348/65 |
| 2012/0010480 | A1* | 1/2012 | Ikai | A61B 1/00045 |
| | | | | 600/302 |
| 2012/0323529 | A1* | 12/2012 | Kessler | B60C 23/0416 |
| | | | | 702/179 |
| 2013/0178702 | A1* | 7/2013 | Tanaka | A61B 5/061 |
| | | | | 600/109 |
| 2013/0207845 | A1* | 8/2013 | Eidloth | G01S 5/0247 |
| | | | | 342/465 |
| 2013/0225981 | A1* | 8/2013 | Hasegawa | A61B 5/073 |
| | | | | 600/424 |
| 2013/0237809 | A1* | 9/2013 | Hasegawa | A61B 1/00016 |
| | | | | 600/424 |
| 2013/0253269 | A1* | 9/2013 | Hasegawa | A61B 5/6805 |
| | | | | 600/109 |
| 2014/0051949 | A1* | 2/2014 | Old | A61B 5/061 |
| | | | | 600/302 |
| 2014/0163316 | A1* | 6/2014 | Koide | A61B 1/0002 |
| | | | | 600/103 |
| 2014/0187918 | A1* | 7/2014 | Higaki | A61B 1/041 |
| | | | | 600/424 |
| 2014/0207374 | A1* | 7/2014 | Taylor, Jr. | G01C 21/206 |
| | | | | 701/470 |
| 2014/0370917 | A1* | 12/2014 | Buchheim | H04W 4/023 |
| | | | | 455/456.1 |
| 2014/0379255 | A1* | 12/2014 | Johnson | A61B 5/0006 |
| | | | | 701/470 |
| 2015/0031954 | A1* | 1/2015 | Kimoto | A61B 1/00006 |
| | | | | 600/118 |
| 2015/0181392 | A1* | 6/2015 | Lee | H04W 4/023 |
| | | | | 455/456.1 |
| 2016/0033635 | A1* | 2/2016 | Hansen | G01S 13/75 |
| | | | | 342/451 |
| 2016/0089009 | A1* | 3/2016 | Takahashi | A61B 1/00045 |
| | | | | 600/103 |
| 2016/0187153 | A1* | 6/2016 | Johnson | G16H 40/63 |
| | | | | 701/500 |
| 2016/0266234 | A1* | 9/2016 | Pearce | G01S 17/86 |
| 2018/0059209 | A1* | 3/2018 | Cuddihy | G01S 5/0226 |
| 2018/0083669 | A1* | 3/2018 | Jeong | H02J 50/10 |
| 2019/0208468 | A1* | 7/2019 | Kaushik | H04W 4/023 |
| 2019/0219678 | A1* | 7/2019 | Miyazawa | G01S 11/06 |
| 2020/0047715 | A1* | 2/2020 | Park | B60R 25/209 |
| 2020/0089272 | A1* | 3/2020 | von Badinski | A61B 5/1455 |

FOREIGN PATENT DOCUMENTS

| | | |
|---|---|---|
| JP | 2016-159021 A | 9/2016 |
| JP | 2016-182215 A | 10/2016 |

OTHER PUBLICATIONS

International Search Report dated Dec. 12, 2017, issued in PCT/JP2017/036043.

* cited by examiner

POSITION DETECTION APPARATUS, POSITION DETECTION SYSTEM, AND POSITION DETECTION METHOD

This application is a continuation of PCT International Application No. PCT/JP2017/036043 filed on Oct. 3, 2017, which designates the United States, incorporated herein by reference, and which claims the benefit of priority from Japanese Patent Application No. 2017-051500, filed on Mar. 16, 2017, incorporated herein by reference.

BACKGROUND

The present disclosure relates to a position detection apparatus, a position detection system, and a position detection method with which the position of a capsule endoscope inserted into a subject is detected.

In the field of endoscopes, there has been a development in capsule endoscopes that are body-insertable apparatuses formed to have a size so as to be insertable into a digestive tract of a subject such as a patient (see, for example, Japanese Laid-open Patent Publication No. 2003-19111). A capsule endoscope is an apparatus having a capturing function and a wireless communication function inside a capsule-shaped casing and, after it is swallowed through the subject's mouth, it sequentially captures the inside of an organ of the subject, acquires image data, and wirelessly transmits it to a receiving device attached to the subject while moving inside the digestive tract due to a peristaltic motion, or the like. The receiving device sequentially receives image data transmitted from the capsule endoscope via a plurality of receiving antennas separately disposed on the body surface of the subject and sequentially stores the image data and the received strength data on the received radio wave in a recording medium. An image processing device fetches the image data and the received strength data stored in the recording medium and causes the display device to display the image having undergone predetermined image processing and the position of the capsule endoscope detected based on the received strength data. Then, a user, such as a doctor, observes the image displayed on the display device and the position with respect to the subject, thereby providing a diagnosis of the subject.

Typically, as for conventional receiving antennas, the location of the receiving antennas is previously fixed such that the receiving antennas are located near an organ through which the capsule endoscope passes. For example, each receiving antenna is fixedly disposed on the jacket worn by the subject during the examination.

SUMMARY

According to the present disclosure, there is provided a position detection apparatus including: a first antenna attached to a predetermined position of a subject and configured to receive a wireless signal transmitted from a medical apparatus inserted into the subject; a second antenna attached to the subject at a different position relative to the first antenna and configured to receive the wireless signal; and a processor including hardware, the processor being configured to: calculate a first received strength of the wireless signal received by the first antenna and a second received strength of the wireless signal received by the second antenna; calculate an attachment position of the second antenna based on the first and the second received strengths; and calculate a position of the medical apparatus based on: the first and the second received strengths; the calculated position of the first antenna; and the calculated position of the second antenna.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
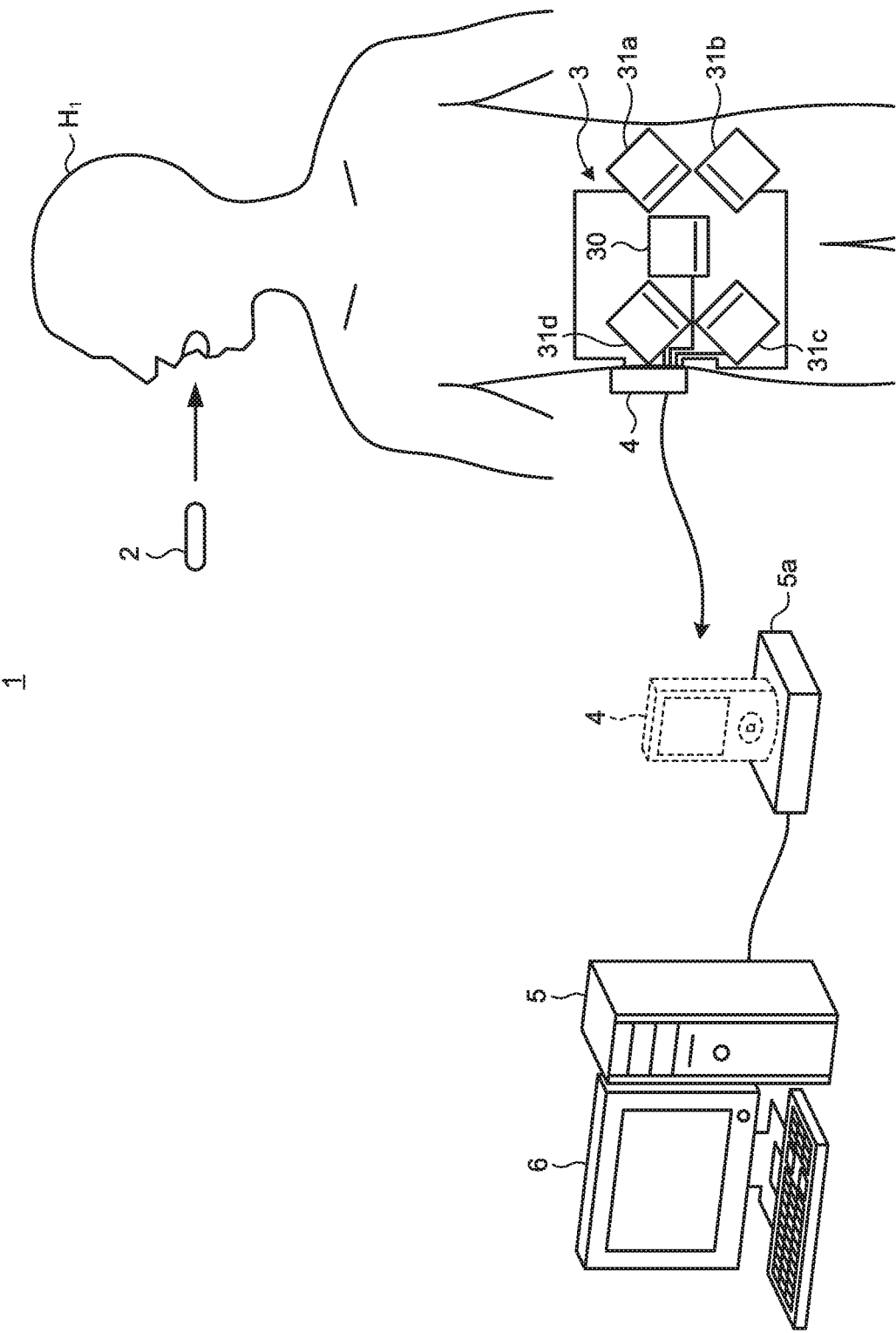
FIG. 1 is a schematic diagram that illustrates a schematic configuration of a capsule endoscope system according to a first embodiment.

A capsule endoscope system using a capsule endoscope, which is a medical apparatus, is explained below as an embodiment. Furthermore, the same components are attached with the same reference numeral in the description of the drawings. Moreover, it should be noted that the drawings are schematic and the relation between members in thickness and width, the ratio between members, and the like, differ from reality.

First Embodiment

FIG. 1 is a schematic diagram that illustrates a schematic configuration of a capsule endoscope system according to a first embodiment. As illustrated in FIG. 1, a capsule endoscope system 1 according to the first embodiment includes: a capsule endoscope 2 that is an image acquiring apparatus that is inserted into a subject $H_1$, captures the inside of the subject $H_1$ to generate an image signal, superimposes it on a wireless signal, and transmits it via a radio wave; a receiving device 4 that receives a wireless signal transmitted from the capsule endoscope 2 via a receiving antenna unit 3 including a plurality of receiving antennas (receiving antennas 30, 31a to 31d) attached to the subject $H_1$; and a processing device 5 that fetches an image signal captured by the capsule endoscope 2 from the receiving device 4 via a cradle 5a, processes the image signal, and generates an image of the inside of the subject $H_1$. Images generated by the processing device 5 are output for display by, for example, a display device 6.

Figure 2:
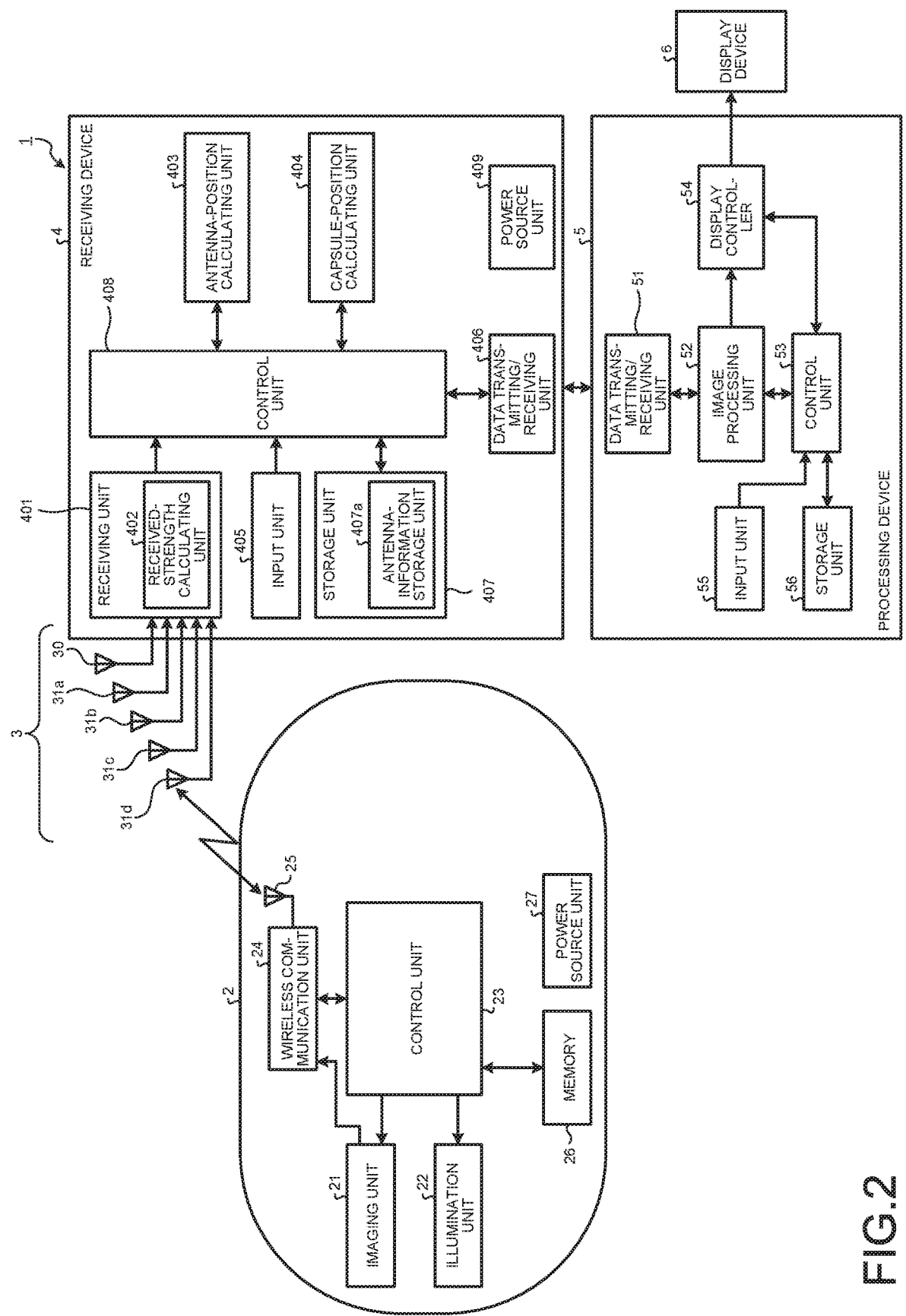
FIG. 2 is a block diagram that illustrates a schematic configuration of the capsule endoscope system according to the first embodiment.

FIG. 2 is a block diagram that illustrates a schematic configuration of the capsule endoscope system according to the first embodiment. The capsule endoscope 2 includes an imaging unit 21, an illumination unit 22, a control unit 23, a wireless communication unit 24, an antenna 25, a memory 26, and a power source unit 27. The capsule endoscope 2 is an apparatus that has each of the above-described components built in a capsule-shaped casing having such a size that it may be swallowed by the subject $H_1$.

The imaging unit 21 includes, for example, an imaging element that generates, from an optical image formed on the light receiving surface, an image signal due to capturing of the inside of the subject $H_1$ and outputs it; and an optical system, such as an objective lens, disposed on the light receiving surface side of the imaging element. The imaging element is formed of a CCD imaging element or a CMOS imaging element, and it has a plurality of pixels arranged in a matrix to receive light from the subject $H_1$ and conducts photoelectric conversion on the light received by the pixel to generate an image signal. The imaging unit 21 reads the pixel value from each horizontal line with regard to the pixels arranged in a matrix and generates an image signal including multiple pieces of line data in which a synchronization signal is attached to each of the horizontal lines.

The illumination unit 22 is configured by using a white LED, or the like, which generates white light that is illumination light. Furthermore, a configuration may be such that, instead of a white LED, white light is generated by combining lights from multiple LEDs or laser light sources having different output wavelength bands, or a configuration may be such that a xenon lamp, a halogen lamp, or the like, is used.

The control unit 23 controls operation processing of each component of the capsule endoscope 2. For example, when the imaging unit 21 performs an imaging process, the imaging unit 21 is controlled to perform the exposure and the reading processes on the imaging element, and the illumination unit 22 is controlled to emit illumination light in accordance with the exposure timing of the imaging unit 21. The control unit 23 is configured by using a general-purpose processor, such as a CPU (Central Processing Unit), or a dedicated processor such as various arithmetic circuits performing a specific function, e.g., ASIC (Application Specific Integrated Circuit).

The wireless communication unit 24 processes an image signal output from the imaging unit 21. The wireless communication unit 24 performs A/D conversion and predetermined signal processing on an image signal output from the imaging unit 21, acquires an image signal in a digital form, superimposes it on a wireless signal together with relevant information, and transmits it from the antenna 25 to an external unit. The relevant information includes, for example, identification information (e.g., serial number) assigned to identify the individuality of the capsule endoscope 2.

The memory 26 stores execution programs and control programs for the control unit 23 to perform various operations. Furthermore, the memory 26 may temporarily store image signals, or the like, on which signal processing has been performed by the wireless communication unit 24. The memory 26 is configured by using a RAM (Random Access Memory), a ROM (Read Only Memory), or the like.

The power source unit 27 includes: a battery that is a button battery, or the like; a power circuit that for example boosts the electric power from the battery; and a power switch that switches the on/off state of the power source unit 27, and it supplies the electric power to each unit of the capsule endoscope 2 after the power switch is turned on. Furthermore, the power switch is a reed switch whose on/off state is switched by for example an external magnetic force; before the capsule endoscope 2 is used (before it is swallowed by the subject $H_1$), it is switched to the on state due to the application of a magnetic force to the capsule endoscope 2 from outside.

After the capsule endoscope 2 described above is swallowed by the subject $H_1$, it moves within a digestive tract of the subject $H_1$ due to a peristaltic motion of an organ, or the like, and sequentially captures an in-vivo site (esophagus, stomach, small intestine, large intestine, and the like) in a predetermined cycle (e.g., the cycle of 0.5 seconds). Then, image signals and relevant information acquired during the imaging operation are sequentially transmitted with radio waves to the receiving device 4 via the receiving antenna unit 3.

The receiving antennas 30, 31a to 31d may be attached to the subject $H_1$ independently from each other. The receiving antenna 30 is an antenna attached to a predetermined position of the subject $H_1$ and serves as a reference for the location of the receiving antennas 31a to 31d (hereafter, the receiving antenna 30 is referred to as a reference antenna 30). As for the reference antenna 30 and the receiving antennas 31a to 31d, as illustrated in FIG. 1, for example, the reference antenna 30 is in the center, and the receiving antennas 31a to 31d are provided around it. Here, the receiving antennas 31a to 31d are disposed to be rotationally symmetric by 180° with respect to the center of the reference antenna 30. The reference antenna 30 is mounted at a predetermined position of the body surface, e.g., an umbilical region. The receiving antennas 31a to 31d are antennas that are attachable to the subject $H_1$ at different positions relative to the reference antenna 30. The reference antenna 30 and the receiving antennas 31a to 31d are implemented by using, for example, loop antennas or dipole antennas.

Figure 3:
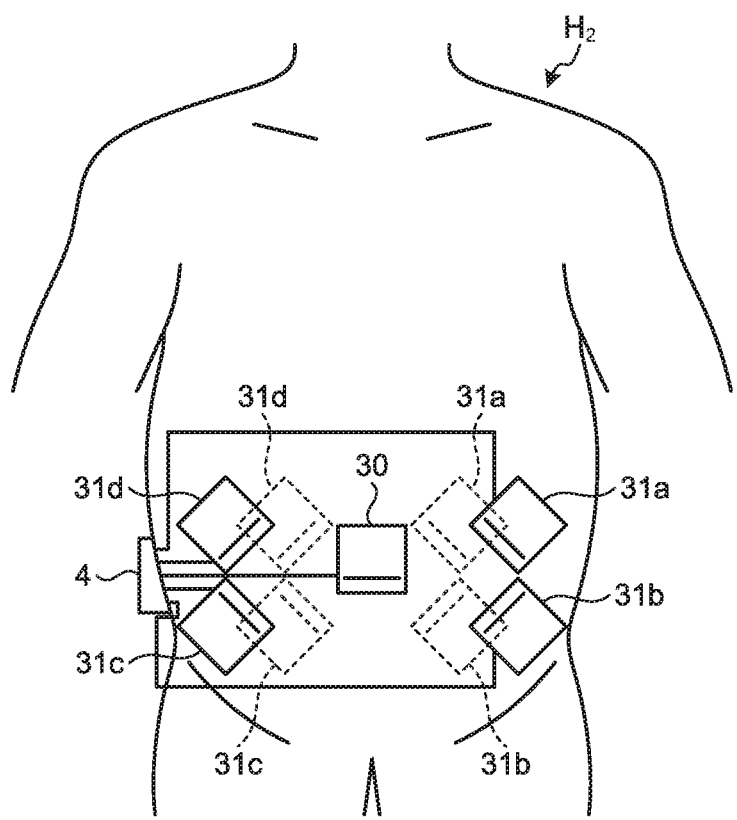
FIG. 3 is a diagram that illustrates a case where receiving antennas are attached to a subject having a physical form different from that of the subject illustrated in FIG. 1.

As the reference antenna 30 and the receiving antennas 31a to 31d are attached to the subject independently from each other, the relative position is different depending on the physical form of the subject. FIG. 3 is a diagram that illustrates a case where the receiving antennas are attached to a subject having a physical form different from that of the subject illustrated in FIG. 1. In FIG. 3, the dashed lines indicate the positions of the receiving antennas 31a to 31d attached to the subject $H_1$. When the reference antenna 30 and the receiving antennas 31a to 31d are attached to a subject $H_2$ having a different size, such as abdominal circumference, as compared to the subject $H_1$ (see FIG. 1), as illustrated in FIG. 3, the positions of the receiving antennas 31a to 31d relative to the reference antenna 30 are different from those in a case where they are attached to the subject $H_1$.

The receiving device 4 includes a receiving unit 401, a received-strength calculating unit 402, an antenna-position calculating unit 403, a capsule-position calculating unit 404, an input unit 405, a data transmitting/receiving unit 406, a storage unit 407, a control unit 408, and a power source unit 409 that supplies electric power to each of the units.

The receiving unit 401 receives image signals and relevant information, wirelessly transmitted from the capsule endoscope 2, via the reference antenna 30 and the receiving antennas 31a to 31d. The receiving unit 401 includes the received-strength calculating unit 402 that calculates the received strength (RSSI: Received Signal Strength Indicator) of image signals received by the receiving antennas 31a to 31d. The receiving unit 401 selects the antenna with the highest received strength from the reference antenna 30 and the receiving antennas 31a to 31d based on the received strengths calculated by the received-strength calculating unit 402 and selects the wireless signal received by the selected antenna for image generation. Furthermore, the receiving unit 401 is configured by using, for example, a CPU, an ASIC, or the like, and executes predetermined signal processing, such as A/D conversion, on the received image signal.

The received-strength calculating unit 402 (first calculating unit) calculates the received strength with regard to each of the reference antenna 30 and the receiving antennas 31a to 31d when the receiving unit 401 receives an image signal. At this point, all the calculated received strengths and the image signal received by the receiving unit 401 may be stored in a related manner in the storage unit 407. The received-strength calculating unit 402 is configured by using a CPU, an ASIC, or the like.

The antenna-position calculating unit 403 (second calculating unit) calculates the positions of the receiving antennas 31a to 31d with the reference antenna 30 as a reference. The antenna-position calculating unit 403 calculates the amount of positional change from the reference location by using the received strength of a radio wave received from the capsule endoscope 2 and corrects the position of the receiving antenna in the reference location based on the amount of change, thereby calculating the position of the receiving antenna. The calculation of the positions of the receiving antennas 31a to 31d by the antenna-position calculating unit 403 is described later. The antenna-position calculating unit 403 is configured by using a CPU, an ASIC, or the like.

The capsule-position calculating unit 404 (third calculating unit) performs calculation to detect the position of the capsule endoscope 2 by using the received strength of each of the reference antenna 30 and the receiving antennas 31a to 31d, input from the receiving unit 401, and the positions of the receiving antennas 31a to 31d calculated by the antenna-position calculating unit 403. The capsule-position calculating unit 404 outputs, to the control unit 408, a detection result of the position of the capsule endoscope 2 as the positional information on the capsule endoscope 2 and stores it in relation to the corresponding image data in the storage unit 407. The capsule-position calculating unit 404 may detect the position of the capsule endoscope 2 by using a known method. The capsule-position calculating unit 404 may detect the position of the capsule endoscope 2 by using, for example, Japanese Laid-open Patent Publication No. 2007-283001. Furthermore, it is possible that each received strength is stored as positional information in the storage unit 407 and the calculation function to detect a position is provided in the processing device 5. Further, the capsule-position calculating unit 404 may detect the position of the capsule endoscope 2 by using a phase, e.g., a difference in phase between different wireless signals.

The capsule-position calculating unit 404 is configured by using a CPU, an ASIC, or the like.

Furthermore, when the processing device 5 has the calculation function to detect a position, i.e., the processing device 5 includes the capsule-position calculating unit 404, the received-strength calculating unit 402 stores a received strength in the storage unit 407 or transmits it to the processing device 5. Then, in the processing device 5, the capsule-position calculating unit 404 detects a position based on received strength information acquired from the receiving device 4.

The input unit 405 is an input device that is used when a user inputs various types of setting information or command information to the receiving device 4. The input unit 405 is a switch, button, or the like, provided on, for example, the operation panel of the receiving device 4.

The data transmitting/receiving unit 406 transmits image signals and relevant information stored in the storage unit 407 to the processing device 5 when it is communicatively connected to the processing device 5. The data transmitting/receiving unit 406 is configured by using a communication interface such as LAN.

The storage unit 407 stores programs for executing various functions by operating the receiving device 4, image signals acquired by the capsule endoscope 2, the number of synchronization signals acquired, and the like. The storage unit 407 is configured by using a RAM, ROM, or the like.

Figure 4:
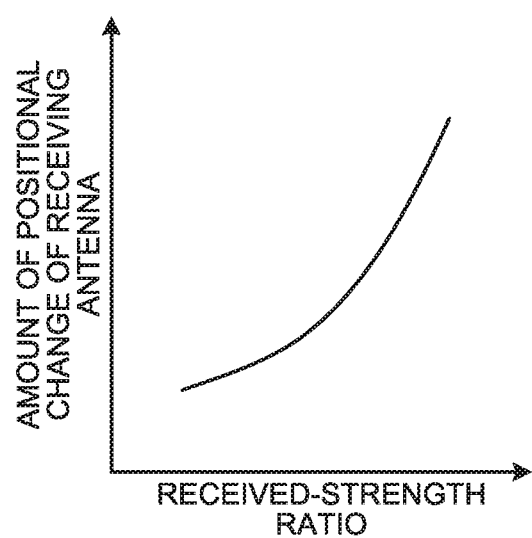
FIG. 4 is a diagram that illustrates the position correction by an antenna-position calculating unit in the capsule endoscope system according to the first embodiment.

The storage unit 407 includes an antenna-information storage unit 407a that stores information for calculating the position of an antenna by the antenna-position calculating unit 403. The antenna-information storage unit 407a stores the reference location of the reference antenna 30 and the receiving antennas 31a to 31d and a correction function for correcting an antenna position. FIG. 4 is a diagram that illustrates the position correction by the antenna-position calculating unit in the capsule endoscope system according to the first embodiment. The antenna-information storage unit 407a stores the correction function illustrated in FIG. 4 for correcting the positions of the receiving antennas 31a to 31d. The correction function illustrated in FIG. 4 is a graph that represents the relation between the received-strength ratio, which is the ratio of the received strength of the receiving antenna (any of the receiving antennas 31a to 31d) to the received strength of the reference antenna 30, and the amount of positional change of the receiving antenna in the reference location. The graph is used when the antenna-position calculating unit 403 calculates the positions of the receiving antennas 31a to 31d. The amount of positional change of the receiving antenna represents the difference between the possible position of the receiving antenna and the position of the target receiving antenna in the reference location.

The control unit 408 controls each component of the receiving device 4. The control unit 408 is configured by using a general-purpose processor such as a CPU or a dedicated processor such as various types of arithmetic circuits for performing a specific function, e.g., an ASIC.

The receiving device 4 of this type is attached to and carried by the subject $H_1$ while the capsule endoscope 2 conducts capturing, e.g., while the capsule endoscope 2 passes through a digestive tract and is discharged after being swallowed by the subject $H_1$. In this period, the receiving device 4 stores an image signal received via the receiving antenna unit 3 in the storage unit 407. Furthermore, the receiving device 4 stores the received strength calculated by the received-strength calculating unit 402 in relation to the corresponding image signal in the storage unit 407.

After capturing by the capsule endoscope 2 is finished, the receiving device 4 is removed from the subject $H_1$ and is set in the cradle 5a (see FIG. 1) coupled to the processing device 5. Thus, the receiving device 4 is communicatively connected to the processing device 5 so as to transmit (download) image signals and relevant information stored in the storage unit 407 to the processing device 5.

The processing device 5 is configured by using, for example, a workstation including the display device 6 such as a liquid crystal display. The processing device 5 includes a data transmitting/receiving unit 51, an image processing unit 52, a control unit 53 that controls each unit in an integrated manner, a display controller 54, an input unit 55, and a storage unit 56.

The data transmitting/receiving unit 51 is an interface connectable to a USB or a communication network such as wired LAN or wireless LAN, and it includes a USB port and a LAN port. According to the embodiment, the data transmitting/receiving unit 51 is coupled to the receiving device 4 via the cradle 5a connected to the USB port so as to transmit/receive data to/from the receiving device 4.

The image processing unit 52 reads a predetermined program stored in the storage unit 56 described later, thereby executing predetermined image processing to generate an in-vivo image corresponding to an image signal input from the data transmitting/receiving unit 51 or an image signal stored in the storage unit 56. The image processing unit 52 is configured by using a CPU, an ASIC, or the like.

The control unit 53 reads various programs stored in the storage unit 56, thereby for example transmitting a command or data to each unit included in the processing device 5 based on a signal input via the input unit 55 or an image signal input from the data transmitting/receiving unit 51 and controlling the overall operation of the processing device 5 in an integrated manner. The control unit 53 is implemented by using a CPU, an ASIC, or the like.

On the image generated by the image processing unit 52, the display controller 54 performs predetermined processing such as gradation processing or decimation on data in accordance with the display range of the image in the display device 6 and then causes the display device 6 to display and output it. The display controller 54 is configured by using a CPU, an ASIC, or the like.

The input unit 55 receives input of information or a command corresponding to the user's operation. The input unit 55 is implemented by using, for example, an input device such as a keyboard, mouse, touch panel, or various switches.

The storage unit 56 stores programs for performing various functions by operating the processing device 5, various types of information used while the program is executed, image signals and relevant information acquired via the receiving device 4, in-vivo images generated by the image processing unit 52, and the like. The storage unit 56 is implemented by using, for example, a semiconductor memory such as a flash memory, RAM, or ROM, a recording medium such as an HDD, MO, CD-R, or DVD-R, and a drive device that drives the recording medium.

Figure 5:
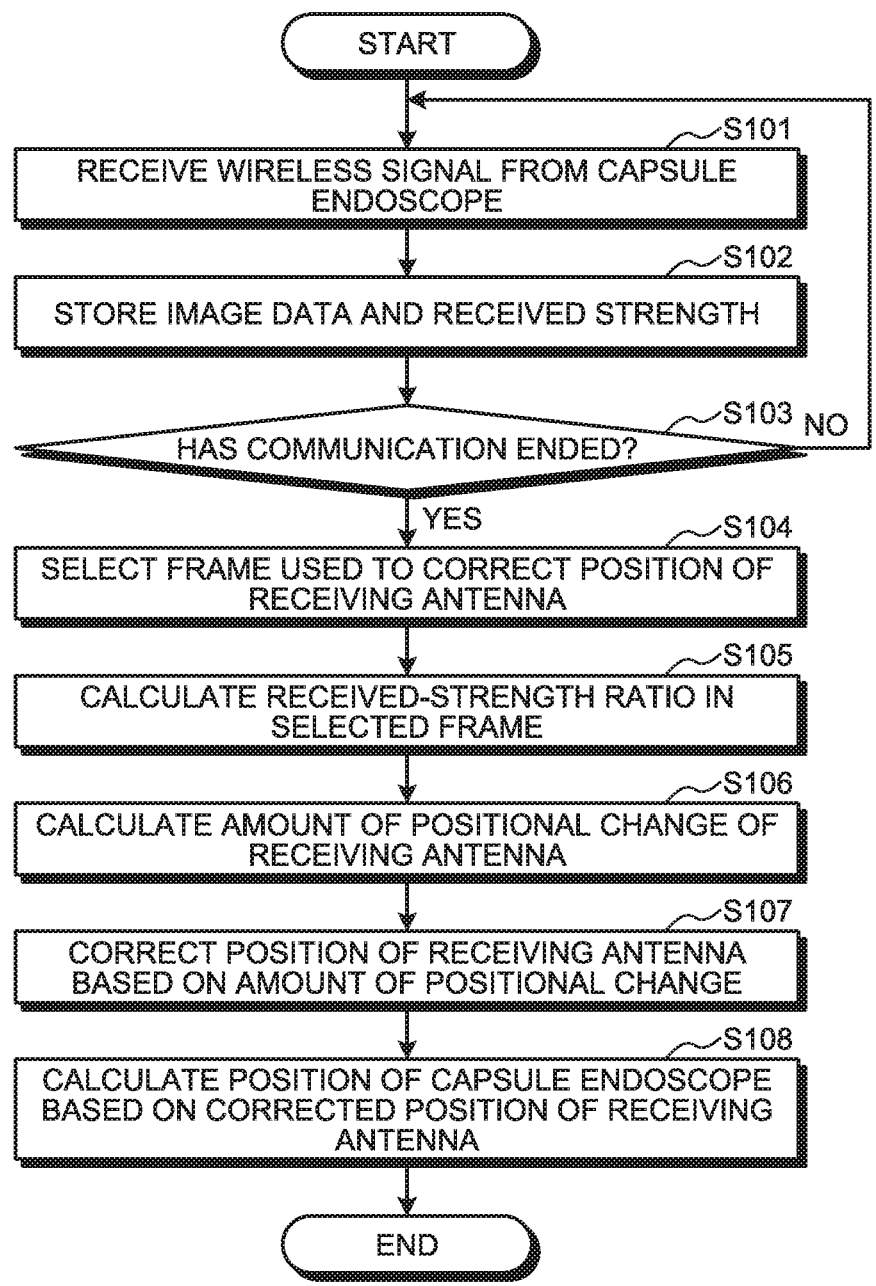
FIG. 5 is a flowchart that illustrates a position detection process performed by a receiving device in the capsule endoscope system according to the first embodiment.

Next, the process performed by the receiving device 4 to detect the position of the capsule endoscope 2 is explained. FIG. 5 is a flowchart that illustrates the position detection process performed by the receiving device in the capsule endoscope system according to the first embodiment. In the following explanation, each unit operates under the control of the control unit 408.

First, at Step S101, the receiving unit 401 receives a wireless signal from the capsule endoscope 2.

At Step S102 subsequent to Step S101, the receiving unit 401 acquires the image data and the received strength from the wireless signal. The received-strength calculating unit 402 calculates the received strength of the wireless signal when it is received by the receiving unit 401. The receiving unit 401 stores the acquired image data and the received strength in a related manner in the storage unit 407.

At Step S103 subsequent to Step S102, the control unit 408 determines whether the communication with the capsule endoscope 2 has ended. For example, the control unit 408 determines whether the communication with the capsule endoscope 2 has ended by determining whether a new wireless signal has been received during a previously set time period after the data having the code indicating the end of the communication is received or the previous wireless signal is received. When it is determined that the communication with the capsule endoscope 2 has not ended (Step S103: No), the control unit 408 returns to Step S101 to receive a new wireless signal. Conversely, when it is determined that the communication with the capsule endoscope 2 has ended (Step S103: Yes), the control unit 408 proceeds to Step S104.

At Step S104 to S107 subsequent to Step S103, the antenna-position calculating unit 403 calculates the position of the receiving antenna. First, at Step S104, the antenna-position calculating unit 403 selects the frame having the received strength used to correct the position of the receiving antenna. According to the first embodiment, the antenna-position calculating unit 403 selects the frame having the highest received strength with regard to the reference antenna 30 from the received strengths of the respective frames stored in the storage unit 407. The antenna-position calculating unit 403 sets the selected frame as the frame used to correct the positions of the receiving antennas 31a to 31d.

At Step S105 subsequent to Step S104, the antenna-position calculating unit 403 calculates the received-strength ratio in the selected frame. Specifically, the antenna-position calculating unit 403 calculates, in the selected frame, the received-strength ratio of the receiving antenna 31a with respect to the received strength of the reference antenna 30, the received-strength ratio of the receiving antenna 31b with respect to the received strength of the reference antenna 30, the received-strength ratio of the receiving antenna 31c with respect to the received strength of the reference antenna 30, and the received-strength ratio of the receiving antenna 31d with respect to the received strength of the reference antenna 30.

Furthermore, in a case where multiple frames with the highest received strength of the reference antenna 30 are selected, the antenna-position calculating unit 403 calculates the received-strength ratio in each frame for each receiving antenna, calculates the average value of the received-strength ratios, and sets the average value as the received-strength ratio of each receiving antenna.

At Step S106 subsequent to Step S105, the antenna-position calculating unit 403 calculates the amount of positional change of each of the receiving antennas 31a to 31d from the reference location by using the received-strength ratio calculated at Step S105 and the correction function (see FIG. 4) stored in the antenna-information storage unit 407a. The antenna-position calculating unit 403 sets the amount of change obtained when the received-strength ratio is input to the correction function illustrated in FIG. 4 as the amount of positional change of the receiving antenna.

At Step S107 subsequent to Step S106, the antenna-position calculating unit 403 corrects the positions of the receiving antennas 31a to 31d with respect to the reference location based on the amount of positional change calculated at Step S106. Specifically, the antenna-position calculating unit 403 refers to the reference location stored in the antenna-information storage unit 407a and moves the position of the receiving antenna corresponding to the reference location by the amount of positional change, thereby determining the position of the receiving antenna. For example, the position of the receiving antenna 31a in the reference location is moved in accordance with the amount of positional change. The moving direction here is previously set, and a movement is made in the direction along, for example, the abdominal circumference. In this manner, the antenna-position calculating unit 403 determines the positions of the receiving antennas 31a to 31d.

At Step S108 subsequent to Step S107, the capsule-position calculating unit 404 calculates the position of the capsule endoscope 2 in each frame based on the position of the reference antenna 30 and the positions of the receiving antennas 31a to 31d corrected at Step S107.

Afterward, for example, the processing device 5 may generate a position detection result indicating the trajectory of the capsule endoscope 2 by using the position of the capsule endoscope 2 in each frame calculated at Step S108 and cause the display device 6 to display the position detection result together with the image captured by the capsule endoscope 2.

According to the above-described first embodiment, the amount of positional change of the receiving antenna in the reference location is calculated based on the received-strength ratio between the reference antenna 30 and each of the receiving antennas 31a to 31d, and the positions of the receiving antennas 31a to 31d are corrected. According to the first embodiment, the position of the capsule endoscope 2 is calculated based on the corrected positions of the receiving antennas 31a to 31d; thus, the position detection of the capsule endoscope is possible with high accuracy even when the relative position of the receiving antennas is changeable.

Furthermore, in the explanation according to the above-described first embodiment, the antenna-position calculating unit 403 selects the highest one from the received strengths of the reference antenna 30 to select the frame for the antenna position correction; however, for example, a frame having a received strength higher than a preset threshold may be selected as the frame for the antenna position correction, or a frame having a symmetric received strength with respect to the reference antenna 30, i.e., a frame in which the received strengths of the receiving antennas 31a to 31d are identical, may be selected as the frame for the antenna position correction. Further, the antenna-position calculating unit 403 may select a frame in which, for example when the receiving antennas 31a, 31b make a pair and the receiving antennas 31c, 31d make a pair, the pairs have a symmetric received strength with respect to the reference antenna, i.e., the received strength of the receiving antennas 31a, 31b and the received strength of the receiving antennas 31c, 31d are identical. Here, the symmetrically arranged pair may be a part of the receiving antennas 31a to 31d. For example, it is possible that the receiving antenna 31a and the receiving antenna 31c make a pair and a frame is selected in which the received strength of the receiving antenna 31a is identical to the received strength of the receiving antenna 31c.

Second Embodiment

Figure 6:
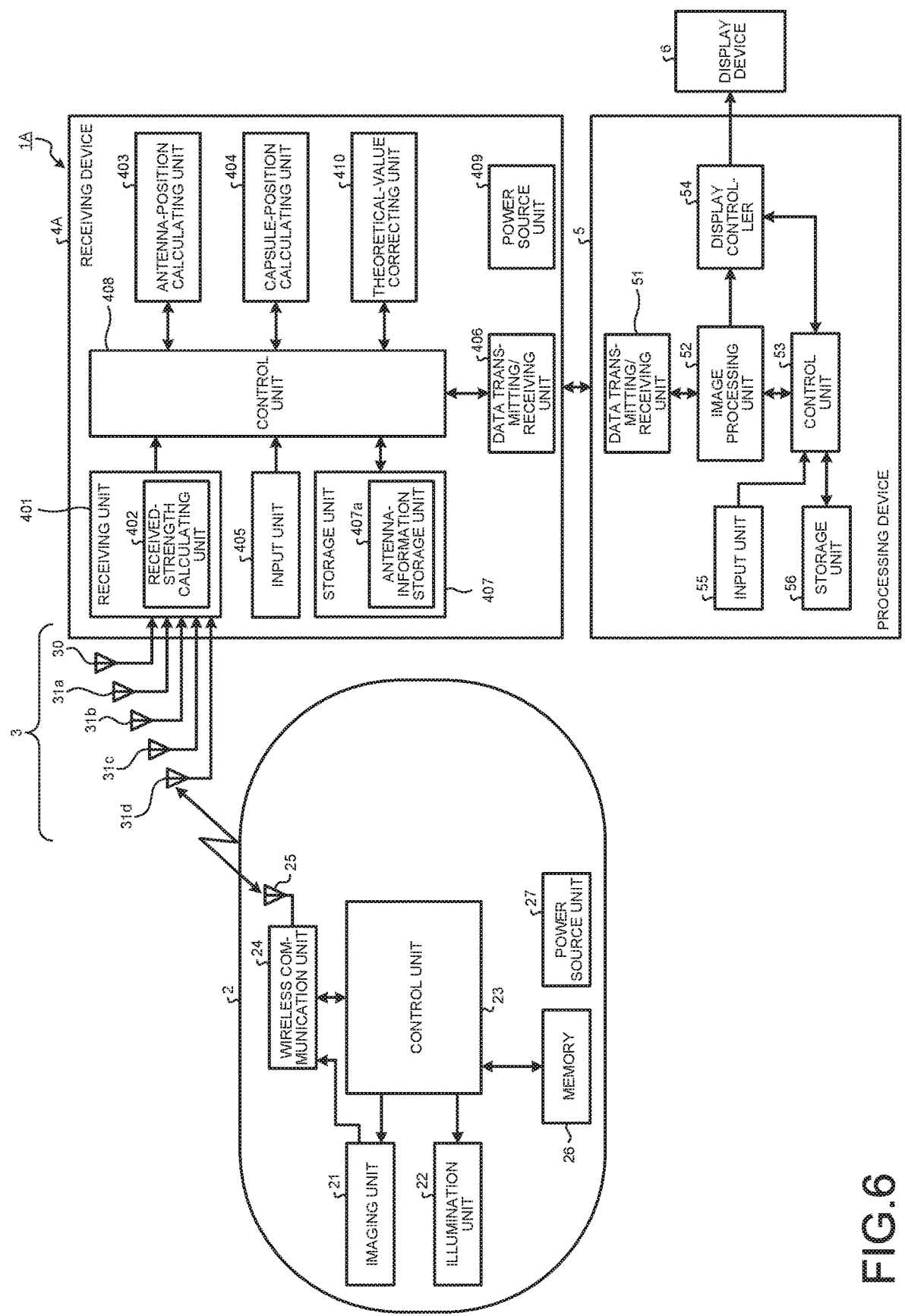
FIG. 6 is a block diagram that illustrates a schematic configuration of a capsule endoscope system according to a second embodiment.

Next, a second embodiment is explained. FIG. 6 is a block diagram that illustrates a schematic configuration of a capsule endoscope system according to the second embodiment.

A capsule endoscope system 1A according to the second embodiment includes the capsule endoscope 2, a receiving device 4A that receives wireless signals transmitted from the capsule endoscope 2 via the receiving antenna unit 3 including the receiving antennas (the reference antenna 30, the receiving antennas 31a to 31d) and attached to the subject $H_1$ (or the subject $H_2$), and the processing device 5 that fetches an image signal, captured by the capsule endoscope 2, from the receiving device 4A via the cradle 5a, processes the image signal, and generates an image inside the subject $H_1$ (or the subject $H_2$). An image generated by the processing device 5 is displayed and output by, for example, the display device 6. According to the second embodiment, only the configuration of the receiving device 4A is different as compared to the configuration of the above-described capsule endoscope system 1.

The receiving device 4A further includes a theoretical-value correcting unit 410 as compared with the configuration of the above-described receiving device 4.

The theoretical-value correcting unit 410 corrects the theoretical received strength data in the reference location stored in the antenna-information storage unit 407a. Specifically, the theoretical received strength is corrected in accordance with the positions (the amounts of positional change) of the receiving antennas 31a to 31d corrected by the antenna-position calculating unit 403. The theoretical-value correcting unit 410 is configured by using a CPU, an ASIC, or the like.

According to the second embodiment, the capsule-position calculating unit 404 calculates the position of the capsule endoscope 2 by using the theoretical received strengths of the reference antenna 30 and the receiving antennas 31a to 31d in the reference location and the received strength obtained from the capsule endoscope 2 inserted into the subject $H_1$.

With reference to FIG. 7A, 7B, and FIG. 8 to FIG. 10, the position calculation of the capsule endoscope 2 is explained. According to the second embodiment, the receiving device 4A calculates the residual sum of squares of the received strength and the theoretical received strength and determines the position and the direction of the capsule endoscope 2 based on the calculated residual sum of squares. An explanation is given below of a process to estimate the position and the direction of the capsule endoscope 2 by the receiving device 4A.

First, an explanation is given of a method for calculating theoretical received strength data that is previously stored in the antenna-information storage unit 407a. First, a predetermined possible existence area T, in which the capsule endoscope 2 may exist, is set in the subject $H_1$ to which the capsule endoscope 2 is inserted depending on a purpose such as examination or diagnosis. The possible existence area T is set in accordance with the physical size of the subject that may exist, and it is an area formed as a cube of 300 mm×300 mm×300 mm as illustrated in for example FIG. 7A. The possible existence area T is set such that the surface of each receiving antenna of the receiving antenna unit 3 coincides with one boundary surface. In the case illustrated in FIG. 7A, the receiving antenna unit 3 is provided on the XY plane that is one boundary surface of the possible existence area T. The position of each of the receiving antennas 31a to 31d is changed in accordance with a calculation result of the antenna-position calculating unit 403.

Figure 7A:
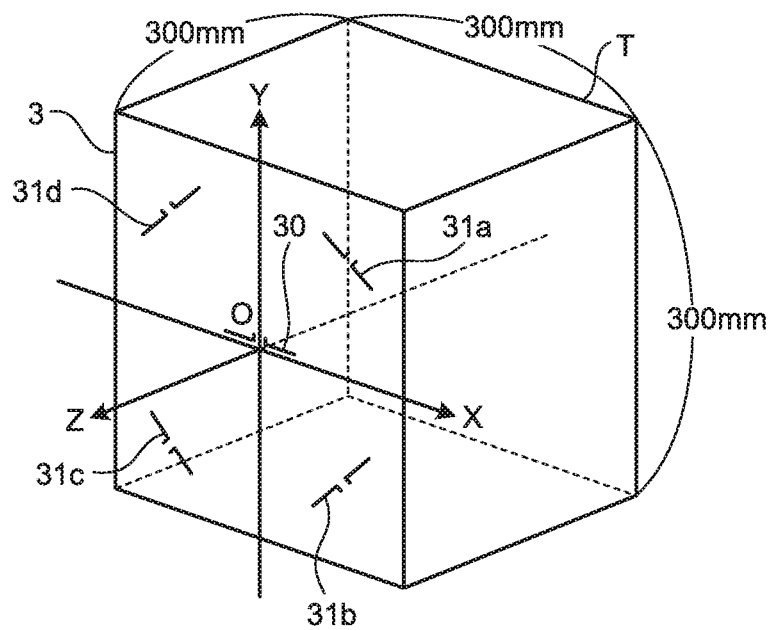
FIG. 7A is a schematic diagram that illustrates the position detection of a capsule endoscope.
Figure 7B:
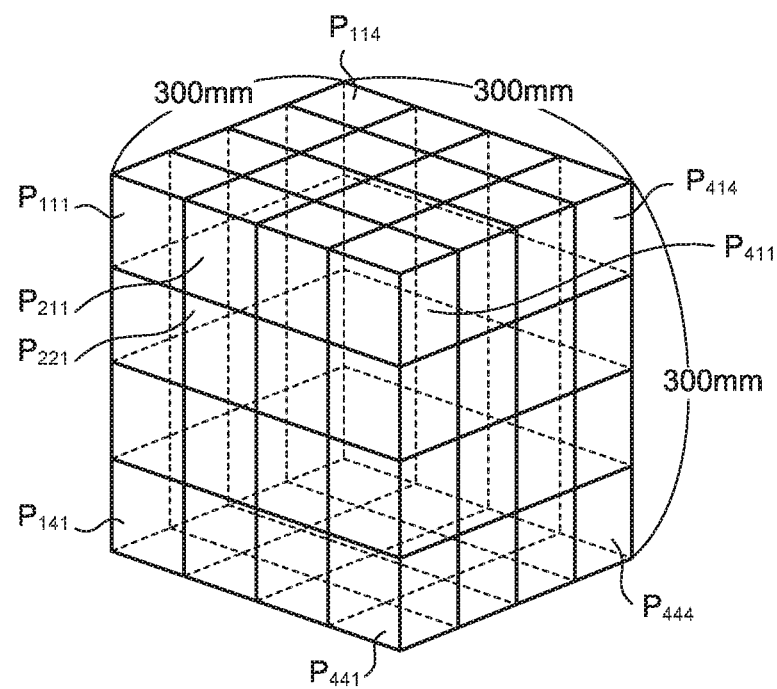
FIG. 7B is a schematic diagram in which an area in FIG. 7A is divided into four parts in each of XYZ directions.

The possible existence area T of the capsule endoscope 2 is divided into partial areas depending on the desired accuracy. FIG. 7B illustrates the case of division into four parts in each axial direction with regard to an orthogonal coordinate system XYZ having, as the origin, the center of the boundary surface where the receiving antenna unit 3 is located and having three axes (X-axis, Y-axis, Z-axis) that are parallel to any side of the possible existence area T and perpendicular to one another. In this case, the possible existence area T is divided into 64 (=4×4×4) partial areas. The respective partial areas are labeled with $P_{111}$, $P_{112}$, $P_{113}$, $P_{114}$, $P_{121}$, $P_{122}$, ..., $P_{144}$, $P_{211}$, $P_{212}$, ..., $P_{444}$. Furthermore, when the capsule endoscope 2 exists in a partial area $P_{ijk}$, it is assumed that it is located at a center $G_{xyz}$ of the partial area $P_{ijk}$.

Figure 8:
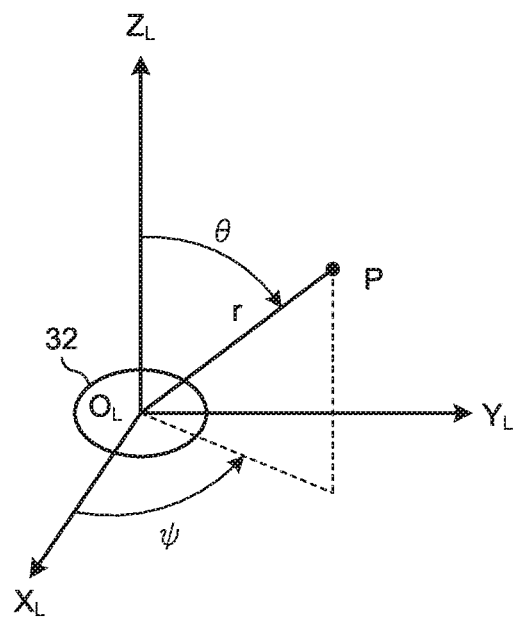
FIG. 8 is a diagram that illustrates a component of an electromagnetic field at an arbitrary position with an antenna (a circular coil is used) of the capsule endoscope as a reference.

In the following explanation, as illustrated in FIG. 8, consideration is given to an orthogonal coordinate system $X_L Y_L Z_L$ where the center of gravity of an antenna 32 disposed inside the capsule endoscope 2 and having a circular loop shape is the origin ($O_L$) and the normal direction of the aperture plane of the circular loop is a $Z_L$-axis. In the orthogonal coordinate system $X_L Y_L Z_L$, the polar coordinate component of the electromagnetic field formed at an arbitrary position P by the current flowing through the antenna 32 is represented by the following Equation (1).

$H_r = (IS/2\pi)(jk/r^2 + 1/r^3)\exp(-jkr)\cos\theta$ $H_\theta = (IS/4\pi)(-k^2/r + jk/r^2 + 1/r^3)\exp(-jkr)\sin\theta$ $E_\varphi = -(j\omega\mu IS/4\pi)(jk/r + 1/r^2)\exp(-jkr)\sin\theta$ (1)

Here, $H_r$ and $H_\theta$ are magnetic-field components, $E_\varphi$ denotes an electric-field component, and I and S denote the current flowing through the antenna 32 and the size of the aperture plane of the circular loop forming the antenna 32. Furthermore, $k=\omega(\varepsilon\mu)^{1/2}$ ($\varepsilon$ is the permittivity, and $\mu$ is the magnetic permeability) is the wave number, and j is the imaginary unit. Here, in Equation (1), the term $r^{-1}$ is a component in the radiation electromagnetic field, the term $r^{-2}$ in the induced electromagnetic field, and the term $r^{-3}$ in the static electromagnetic field.

When the electromagnetic field generated by the antenna 32 provided inside the capsule endoscope 2 has a high frequency and the capsule endoscope 2 and each of the receiving antennas (the reference antenna 30, the receiving antennas 31a to 31d) attached to the body surface of the subject $H_1$ are apart from each other in a sufficient distance as illustrated in FIG. 1, the component of the radiation electromagnetic field is largest with regard to the electromagnetic field (electromagnetic wave) reaching each of the receiving antennas. Therefore, the components of the static electromagnetic field and of the induced electromagnetic field are smaller than the component of the radiation electromagnetic field, and they are ignorable. Thus, Equation (1) is changed into the following Equation (2).

$H_r = 0$ $H_\theta = (IS/4\pi)(-k^2/r)\exp(-jkr)\sin\theta$ $E_\varphi = -(j\omega\mu IS/4\pi)(jk/r)\exp(-jkr)\sin\theta$ (2)

When each of the receiving antennas attached to the body surface of the subject $H_1$ is an electric-field detection antenna that detects an electric field, the equation necessary for the detection in Equation (2) is the electric field $E_\varphi$. Therefore, by the use of alternating-current theory, the instantaneous value of the electric field $E_\varphi$ is obtained by multiplying both sides of the electric field $E_\varphi$ in Equation (2) by $\exp(j\omega t)$ and extracting the real part.

$E\varphi\exp(j\omega t) = -(j\omega\mu IS/4\pi)(jk/r)\exp(-jkr)\sin\theta\exp(j\omega t) =$ (3)
$(\omega\mu ISk/4\pi r)(\cos U + j\sin U)\sin\theta$ Here, $U=\omega t-kr$. Here, when the real part in Equation (3) is extracted, an instantaneous value $E'_\varphi$ of the electric field is as follows.

$E'_\varphi = (\omega\mu ISk/4\pi r)\cos U \sin\theta$ (4)

Furthermore, when Equation (4) is represented by using the orthogonal coordinate system $X_L Y_L Z_L$, components $E_{Lx}$, $E_{Ly}$, $E_{Lz}$ are as in the following Equation (5).

$E_{Lx} = E_\varphi' \sin\varphi = (\omega\mu ISk/4\pi r^2)\cos U \cdot (-y_L)$ $E_{Ly} = E_\varphi' \cos\varphi = (\omega\mu ISk/4\pi r^2)\cos U \cdot x_L$ $E_{Lz} = 0$ (5)

Figure 9:
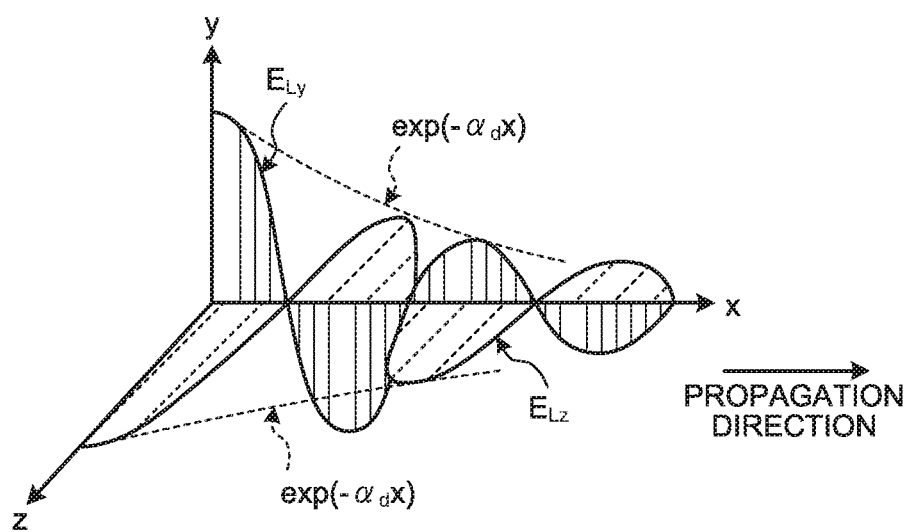
FIG. 9 is a diagram that illustrates the behavior of the electromagnetic field attenuating while propagating through a medium.
Figure 10:
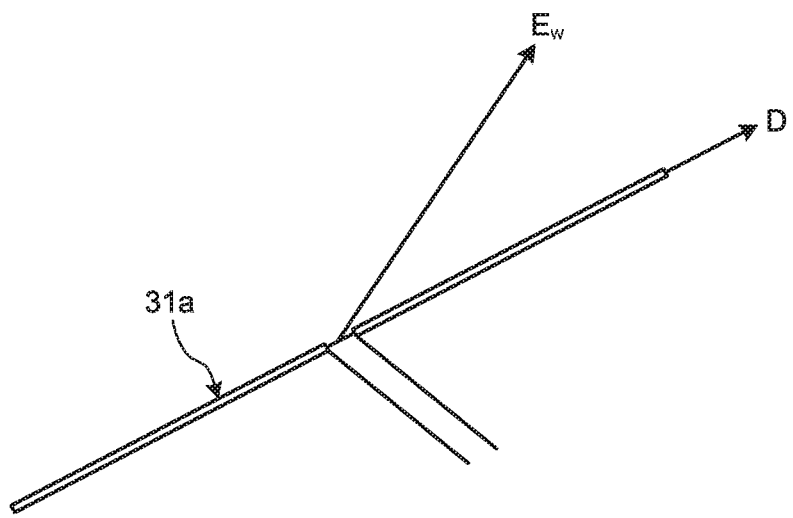
FIG. 10 is a diagram that illustrates the relation between the electric field generated by the capsule endoscope and the direction of one receiving antenna of a receiving antenna unit.

When an electromagnetic wave propagates through a medium, the energy of the electromagnetic wave is absorbed by the medium during propagation due to the property (conductivity, and the like) of the medium, as illustrated in FIG. 9. As the electromagnetic wave propagates in, for example, the x-direction, it attenuates in an exponential fashion with an attenuation factor $\alpha_d$, which is representable by the following Equation (6).

$A_r = \exp(-\alpha_d x)$ $\alpha_d = (\omega^2\varepsilon\mu/2)^{1/2}[(1+\kappa^2/(\omega^2\varepsilon^2))^{1/2} - 1]^{1/2}$ (6)

Here, $\varepsilon=\varepsilon_o\varepsilon_r$ ($\varepsilon_o$: the permittivity in a vacuum, $\varepsilon_r$: the relative permittivity), $\mu=\mu_o\mu_r$ ($\mu_o$: the magnetic permeability in a vacuum, $\mu_r$: the relative magnetic permeability), $\omega$ is the angular frequency, and $\kappa$ is the conductivity.

Therefore, the components $E_{Lx}$, $E_{Ly}$, $E_{Lz}$ of the orthogonal coordinate system $X_L Y_L Z_L$ for the instantaneous value $E_L$ of the electric field when consideration is given to the in-vivo property are as follows.

$E_{Lx} = A_r E_\varphi' \sin\varphi = \exp(-\alpha_d r)(\omega\mu ISk/4\pi r^2)\cos U \cdot (-y_L)$ $E_{Ly} = A_r E_\varphi' \cos\varphi = \exp(-\alpha_d r)(\omega\mu ISk/4\pi r^2)\cos U \cdot x_L$ $E_{Lz} = 0$ (7)

Furthermore, in the orthogonal coordinate system $X_L Y_L Z_L$ based on the antenna 32 of the capsule endoscope 2, the equation for converting the position P ($X_L, Y_L, Z_L$) into an orthogonal coordinate system $X_W Y_W Z_W$ where the center (O in FIG. 7A) of the receiving antenna unit 3 attached to the subject $H_1$ is the origin is:

$$\begin{pmatrix} x_{LP} \\ y_{LP} \\ z_{LP} \end{pmatrix} = R^{-1} \left[ \begin{pmatrix} x_{WP} \\ y_{WP} \\ z_{WP} \end{pmatrix} - \begin{pmatrix} x_{WG} \\ y_{WG} \\ z_{WG} \end{pmatrix} \right] = \begin{pmatrix} R_{00} & R_{01} & R_{02} \\ R_{10} & R_{11} & R_{12} \\ R_{20} & R_{21} & R_{22} \end{pmatrix} \left[ \begin{pmatrix} x_{WP} \\ y_{WP} \\ z_{WP} \end{pmatrix} - \begin{pmatrix} x_{WG} \\ y_{WG} \\ z_{WG} \end{pmatrix} \right] \quad (8)$$

Here, $(x_{WP}, y_{WP}, z_{WP})$ and $(x_{WG}, y_{WG}, z_{WG})$ represent the position P and the position of the antenna 32, respectively, in the coordinate system $X_W Y_W Z_W$. Furthermore, the right side R of Equation (8) represents the rotation matrix of the orthogonal coordinate system $X_W Y_W Z_W$ and the orthogonal coordinate system $X_L Y_L Z_L$, and it is obtained by the following equation.

$$\begin{pmatrix} R_{00} & R_{10} & R_{20} \\ R_{01} & R_{11} & R_{21} \\ R_{02} & R_{12} & R_{22} \end{pmatrix} = \begin{pmatrix} \cos\alpha\cos\beta & -\sin\alpha & \cos\alpha\cos\beta \\ \sin\alpha\cos\beta & \cos\alpha & \sin\alpha\sin\beta \\ -\sin\beta & 0 & \cos\beta \end{pmatrix} \quad (9)$$

Here, $\alpha$ is the rotation angle around the Z-axis, and $\beta$ is the rotation angle around the Y-axis.

Therefore, the electric field $E_W$ at the arbitrary position P $(x_{WP}, y_{WP}, z_{WP})$ of the orthogonal coordinate system $X_W Y_W Z_W$, in which the center (O in FIG. 7A) of the receiving antenna unit 3 attached to the subject $H_1$ is the origin, is $$E_W = \begin{pmatrix} E_{Wx} \\ E_{Wy} \\ E_{Wz} \end{pmatrix} = R \begin{pmatrix} E_{Lx} \\ E_{Ly} \\ E_{Lz} \end{pmatrix} = \begin{pmatrix} R_{00} & R_{10} & R_{20} \\ R_{01} & R_{11} & R_{21} \\ R_{02} & R_{12} & R_{22} \end{pmatrix} \begin{pmatrix} E_{Lx} \\ E_{Ly} \\ E_{Lz} \end{pmatrix} \quad (10)$$

and, Equation (11) for the electric field $E_W$ described below is obtained by substituting Equations (7) to (9) into Equation (10).

$$\begin{pmatrix} E_{Wx} \\ E_{Wy} \\ E_{Wz} \end{pmatrix} = \frac{k_1}{r^2} e^{-\alpha_d r} \begin{pmatrix} 0 & (z_{WP}-z_{WG}) & -(y_{WP}-y_{WG}) \\ -(z_{WP}-z_{WG}) & 0 & (x_{WP}-x_{WG}) \\ (y_{WP}-y_{WG}) & -(x_{WP}-x_{WG}) & 0 \end{pmatrix} \begin{pmatrix} g_x \\ g_y \\ g_z \end{pmatrix} \quad (11)$$

Here, $k_1$ is a constant, and a vector $(g_x, g_y, g_z)$ represents a direction g of the antenna 32. According to the second embodiment, the direction $(g_x, g_y, g_z)$ of the antenna 32 is also previously set together with the position of the capsule endoscope 2, and the theoretical received strength of each receiving antenna when the capsule endoscope 2 is located at a predetermined area and at a predetermined direction is calculated. The direction of the antenna 32 may be set by 1° with respect to, for example, the horizontal axis and the vertical axis in accordance with the desired accuracy.

Furthermore, an electromotive force $V_{ta}$ that is detected when the electric field $E_W$ generated by the antenna 32 is received by the receiving antenna 31a included in the receiving antenna unit 3 is calculable with the following Equation (12) by using the inner product of the electric field $E_W$ and a vector $D_a = (D_{xa}, D_{ya}, D_{za})$ (see FIG. 10) representing the direction of the receiving antenna 31a of the receiving antenna unit 3 in the coordinate system with the subject $H_1$ as a reference.

$$V_{ta} = k_2 (E_{Wx} D_{xa} + E_{Wy} D_{ya} + E_{Wz} D_{za}) \quad (12)$$

Here, $k_2$ is a constant. In the same manner, with regard to each of the receiving antennas of the receiving antenna unit 3 attached to the body of the subject $H_1$, electromotive forces $V_{tb}, \ldots, V_{td}$ when received by the receiving antenna 31b to the receiving antenna 31d are also obtained.

A theoretical received strength $V_{ti}$ of reception by each receiving antenna is calculated as described above, and it is stored as theoretical received strength data in the antenna-information storage unit 407a for the center position $G_{xyz}$ of each divided area.

The capsule-position calculating unit 404 calculates the residual sum of squares of the received strength of reception by each receiving antenna and the theoretical received strength, which is calculated and stored as theoretical received strength data in the antenna-information storage unit 407a as described above, for each direction g of the antenna 32 with regard to the center position G of each area where the capsule endoscope 2 may exist. When the received strength of reception by the receiving antenna is $V_{mi}$ (i is the number of the receiving antenna), the residual sum of squares S is calculable with the following equation.

$$S = \sum_{i=a}^{e} (V_{ti} - V_{mi})^2 = (V_{ta} - V_{ma})^2 + (V_{tb} - V_{mb})^2 + \ldots + (V_{th} - V_{me})^2 \quad (13)$$

The capsule-position calculating unit 404 determines that the center position G of the capsule endoscope 2 and the direction g of the antenna 32 that are the minimum among the residual sums of squares S calculated as described above are the position and the direction of the capsule endoscope 2.

According to the second embodiment, the area where the capsule endoscope 2 may exist is divided into multiple small areas, and the theoretical received strength $V_{ti}$ corresponding to the direction of the capsule endoscope 2 is previously stored for each divided area; thus, the processing load for calculating the theoretical received strength $V_{ti}$ may be reduced. Moreover, as the position and the direction of the capsule endoscope 2 that has captured image data are determined based on the numerical value obtained by simple arithmetic processing that is the residual sum of squares of the stored theoretical received strength $V_{ti}$ and the actual received strength $V_{mi}$ of reception by each receiving antenna; thus, the speed of the position estimation process may be increased.

The capsule-position calculating unit 404 is capable of determining the position and the direction of the capsule endoscope 2 inside the subject $H_1$ as described above; furthermore, the position and the direction of the capsule endoscope 2 may be obtained by iterative refinement by using the Gauss-Newton method as disclosed in, for example, Japanese Laid-open Patent Publication No. 2007-283001.

Figure 11:
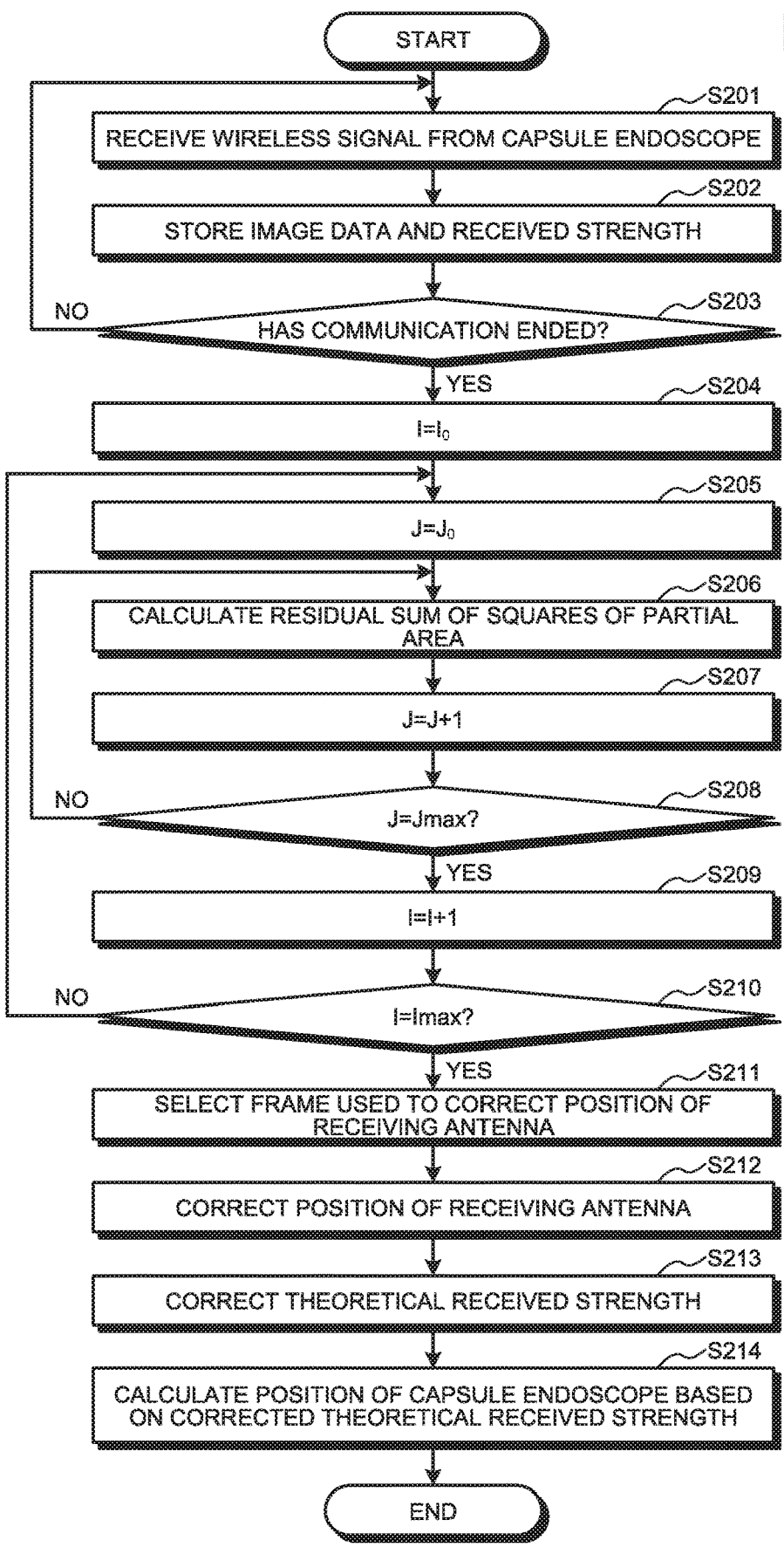
FIG. 11 is a flowchart that illustrates a position detection process performed by the receiving device in the capsule endoscope system according to the second embodiment.

Next, the process to detect the position of the capsule endoscope 2 as performed by the receiving device 4A is explained. FIG. 11 is a flowchart that illustrates the position detection process performed by the receiving device in the capsule endoscope system according to the second embodiment.

First, at Step S201, the receiving unit 401 receives a wireless signal from the capsule endoscope 2. The receiving unit 401 acquires the image data and the received strength from the wireless signal and stores the image data and the received strength in a related manner in the storage unit 407 (Step S202).

At Step S203 subsequent to Step S202, the control unit 408 determines whether the communication with the capsule endoscope 2 has ended. In the same manner as the above-described first embodiment, when it is determined that the communication with the capsule endoscope 2 has not ended (Step S203: No), the control unit 408 returns to Step S201 to receive a new wireless signal. Conversely, when it is determined that the communication with the capsule endoscope 2 has ended (Step S203: Yes), the control unit 408 proceeds to Step S204.

At Step S204 to Step S210, the capsule-position calculating unit 404 calculates the residual sum of squares of the theoretical strength and each of the received strengths of reception by the reference antenna 30 and the receiving antennas 31a to 31d with regard to multiple sets of image data (frames) stored in the storage unit 407. Each frame is attached with a frame number.

At Step S204, the capsule-position calculating unit 404 sets a counter I (I is a natural number), which identifies a frame number, to $I_0$. The default value $I_0$ corresponds to, for example, the first (the first in chronological order) frame in the image data stored in the storage unit 407.

At Step S205 subsequent to Step S204, the capsule-position calculating unit 404 sets a counter J (J is a natural number), which identifies the partial area (see FIG. 7B) for which the residual sum of squares is calculated, to $J_0$ with regard to the frame number I. The default value $J_0$ corresponds to, for example, the first (the first in chronological order) partial area in the set partial areas.

At Step S206 subsequent to Step S205, the capsule-position calculating unit 404 calculates the residual sum of squares of the theoretical received strength and the received strength of reception by each of the reference antenna 30 and the receiving antennas 31a to 31d with regard to the J-th partial area in the frame corresponding to the counter I. The theoretical received strength here is the strength (reference received strength) calculated based on the received strength in the previously set reference location. The capsule-position calculating unit 404 calculates the residual sum of squares with regard to each of the receiving antennas (the reference antenna 30 and the receiving antennas 31a to 31d).

The capsule-position calculating unit 404 increments the counter J by 1 after calculating the residual sum of squares with regard to the J-th partial area (Step S207). This means that the process to calculate the residual sum of squares proceeds to the next partial area.

At Step S208 subsequent to Step S207, the capsule-position calculating unit 404 determines whether the counter J has reached a maximal value Jmax. When it is determined that the counter J has not reached Jmax, i.e., smaller than Jmax (Step S208: No), the capsule-position calculating unit 404 returns to Step S206 to calculate the residual sum of squares for the partial area corresponding to the counter J. Conversely, when it is determined that the counter J has reached Jmax (Step S208: Yes), the capsule-position calculating unit 404 proceeds to Step S209.

Here, the capsule-position calculating unit 404 determines that the partial area having the minimum residual sum of squares in the frame corresponding to the counter I is the position of the capsule endoscope 2 in the frame. The capsule-position calculating unit 404 relates the determined partial area and the theoretical received strength of the partial area and obtains it as a position detection result of the frame corresponding to the counter I.

At Step S209, the capsule-position calculating unit 404 increments the counter I by 1. This means that the process to calculate the residual sum of squares proceeds to the next frame.

At Step S210 subsequent to Step S209, the capsule-position calculating unit 404 determines whether the counter I has reached a maximal value Imax. When it is determined that the counter I has not reached Imax, i.e., smaller than Imax (Step S210: No), the capsule-position calculating unit 404 returns to Step S205 to calculate the residual sum of squares in the frame corresponding to the counter I. Conversely, when it is determined that the counter I is larger than Imax (Step S210: Yes), the antenna-position calculating unit 403 proceeds to Step S211.

The process from Step S204 to Step S210 described above outputs the position detection result in which the minimum residual sum of squares is related to each frame.

At Step S211, the antenna-position calculating unit 403 selects a frame used to correct the position of the receiving antenna. According to the second embodiment, the antenna-position calculating unit 403 selects a frame having the minimum residual sum of squares among the residual sums of squares related to the respective frames.

In this manner, the antenna-position calculating unit 403 selects a frame used for correction based on the difference between the theoretical received strength and the received strength of each receiving antenna. The antenna-position calculating unit 403 sets the selected frame as a frame used to correct the positions of the receiving antennas 31a to 31d.

At Step S212 subsequent to Step S211, the antenna-position calculating unit 403 corrects the positions of the receiving antennas 31a to 31d by using the received strength of the selected frame. In the same manner as in the above-described first embodiment, the antenna-position calculating unit 403 calculates the received-strength ratio of each receiving antenna with respect to the received strength of the reference antenna 30 in the selected frame and, by using the calculated received-strength ratio and the correction function (see FIG. 4) stored in the antenna-information storage unit 407a, calculates the amount of positional change of each of the receiving antennas 31a to 31d from the reference position. Then, the antenna-position calculating unit 403 corrects the positions of the receiving antennas 31a to 31d with respect to the reference location based on the calculated amount of positional change. Furthermore, the amount of positional change of the receiving antenna may be calculated by using not only a correction function but also, for example, a look-up table.

At Step S213 subsequent to Step S212, the theoretical-value correcting unit 410 corrects the theoretical received strength based on the positions of the receiving antennas 31a to 31d corrected at Step S212. The theoretical-value correcting unit 410 corrects the theoretical received strength based on the corrected location of the receiving antennas.

At Step S214 subsequent to Step S213, the capsule-position calculating unit 404 calculates the position of the capsule endoscope 2 in each frame by using the received strength of each receiving antenna and the theoretical received strength corrected at Step S213. At this time, the capsule-position calculating unit 404 calculates the residual sum of squares in the same manner as in the above-described Step S204 to Step S210, extracts the partial area having the minimum residual sum of squares in each frame, and determines the position of the capsule endoscope 2 in each frame.

Afterward, for example, the processing device 5 may generate a position detection result representing the trajectory of the capsule endoscope 2 by using the position of the capsule endoscope 2 in each frame calculated at Step S214 and cause the display device 6 to display the position detection result together with the image captured by the capsule endoscope 2.

According to the above-described second embodiment, the frame for correcting the positions of the receiving antennas 31a to 31d is selected based on a position detection result of the capsule endoscope 2, and the amount of positional change of the receiving antenna in the reference location is calculated based on the received-strength ratio between the reference antenna 30 and each of the receiving antennas 31a to 31d in the selected frame so that the positions of the receiving antennas 31a to 31d are corrected. According to the second embodiment, the position of the capsule endoscope 2 is calculated based on the corrected positions of the receiving antennas 31a to 31d, whereby the position of the capsule endoscope may be detected with high accuracy even when the relative position of the receiving antennas is changeable.

Furthermore, in the explanation according to the above-described second embodiment, the residual sum of squares is calculated; however, instead of the residual sum of squares, an evaluation value, e.g., an evaluation value based on the received strength of a receiving antenna and a theoretical received strength, may be calculated by using an evaluation function using, for example, the average value of differences or the absolute value of a difference.

Third Embodiment

Next, a third embodiment is explained. A capsule endoscope system according to the third embodiment is the same as the above-described capsule endoscope system 1A.

Figure 12:
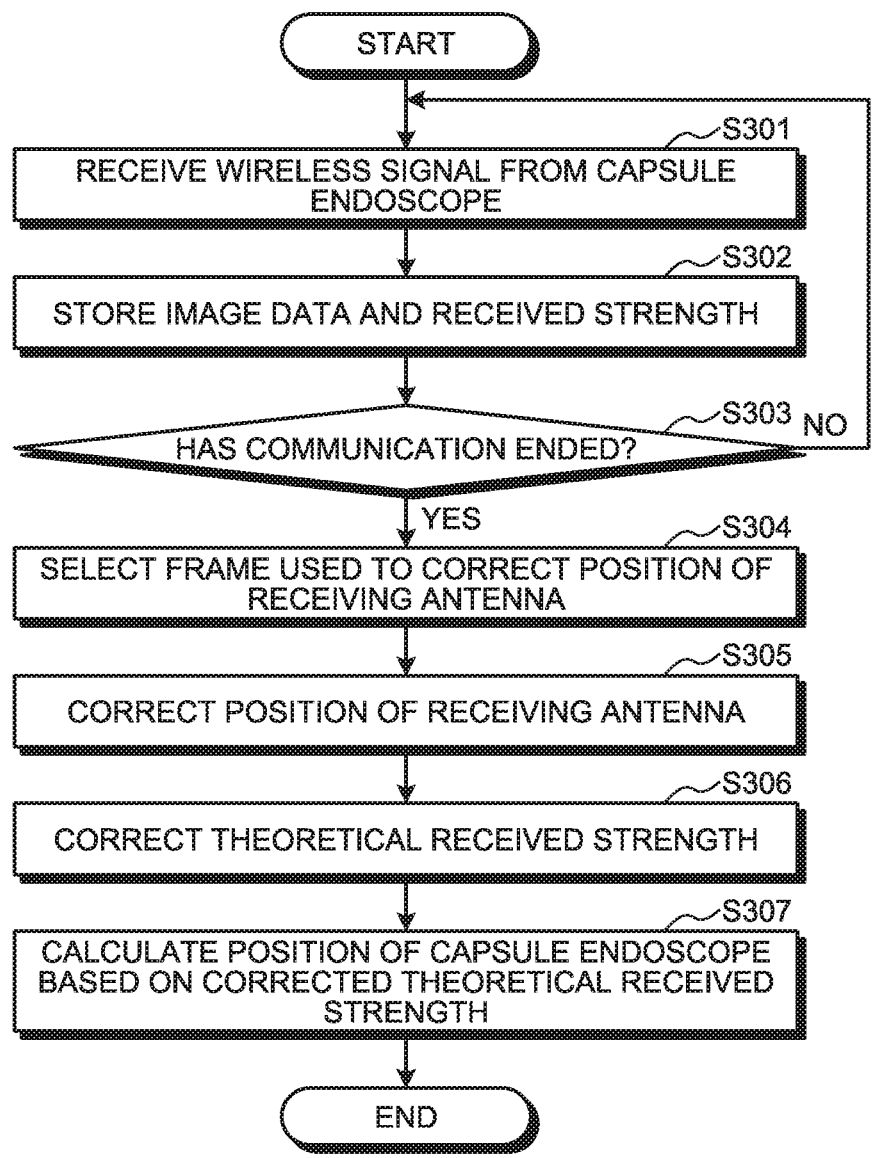
FIG. 12 is a flowchart that illustrates a position detection process performed by the receiving device in a capsule endoscope system according to a third embodiment.

In the third embodiment, an explanation is given of the process to detect the position of the capsule endoscope 2 as performed by the receiving device 4A. FIG. 12 is a flowchart that illustrates the position detection process performed by the receiving device in the capsule endoscope system according to the third embodiment.

First, at Step S301, the receiving unit 401 receives a wireless signal from the capsule endoscope 2. The receiving unit 401 acquires the image data and the received strength from the wireless signal and stores the image data and the received strength in a related manner in the storage unit 407 (Step S302).

At Step S303 subsequent to Step S302, the control unit 408 determines whether the communication with the capsule endoscope 2 has ended. In the same manner as in the above-described first embodiment, when it is determined that the communication with the capsule endoscope 2 has not ended (Step S303: No), the control unit 408 returns to Step S301 to receive a new wireless signal. Conversely, when it is determined that the communication with the capsule endoscope 2 has ended (Step S303: Yes), the control unit 408 proceeds to Step S304.

At Step S304, the antenna-position calculating unit 403 selects the frame used to correct the position of the receiving antenna. According to the third embodiment, the antenna-position calculating unit 403 selects the frame with the highest received strength with regard to the reference antenna 30 among the received strengths of the respective frames stored in the storage unit 407. The antenna-position calculating unit 403 sets the selected frame as the frame used to correct the positions of the receiving antennas 31a to 31d.

At Step S305 subsequent to Step S304, the antenna-position calculating unit 403 corrects the positions of the receiving antennas 31a to 31d by using the received strength in the selected frame. In the same manner as in the above-described first embodiment, the antenna-position calculating unit 403 calculates the received-strength ratio of each receiving antenna with respect to the received strength of the reference antenna 30 in the selected frame and, by using the calculated received-strength ratio and the correction function (see FIG. 4) stored in the antenna-information storage unit 407a, calculates the amount of positional change of each of the receiving antennas 31a to 31d from the reference position. Then, the antenna-position calculating unit 403 corrects the positions of the receiving antennas 31a to 31d with respect to the reference location based on the calculated amount of positional change.

At Step S306 subsequent to Step S305, the theoretical-value correcting unit 410 corrects the theoretical received strength based on the positions of the receiving antennas 31a to 31d corrected at Step S305. The theoretical-value correcting unit 410 corrects the theoretical received strength based on the corrected location of the receiving antennas.

At Step S307 subsequent to Step S306, the capsule-position calculating unit 404 calculates the position of the capsule endoscope 2 in each frame by using the received strength of each receiving antenna and the theoretical received strength corrected at Step S306. At this time, the capsule-position calculating unit 404 calculates the residual sum of squares in the same manner as in the above-described Step S204 to Step S210, extracts the partial area having the minimum residual sum of squares in each frame, and determines the position of the capsule endoscope 2 in each frame.

Afterward, for example, the processing device 5 may generate a position detection result representing the trajectory of the capsule endoscope 2 by using the position of the capsule endoscope 2 in each frame calculated at Step S307 and cause the display device 6 to display the position detection result together with the image captured by the capsule endoscope 2.

As described above, according to the third embodiment, the frame used to correct the positions of the receiving antennas 31a to 31d is selected in the same manner as in the above-described first embodiment, and the position of the capsule endoscope 2 is calculated based on the corrected position of the receiving antenna in the same manner as in the second embodiment. According to the third embodiment, the position of the capsule endoscope 2 is calculated based on the corrected positions of the receiving antennas 31a to 31d; thus, the position detection of the capsule endoscope is possible with high accuracy even when the relative position of the receiving antennas is changeable.

Fourth Embodiment

Next, a fourth embodiment is explained. A capsule endoscope system according to the fourth embodiment is the same as the above-described capsule endoscope system 1.

According to the fourth embodiment, multiple reference location patterns are stored in the antenna-information storage unit 407a and, based on the input physical form information on the subject $H_1$ (or the subject $H_2$), the reference location pattern to be used is selected.

Figure 13:
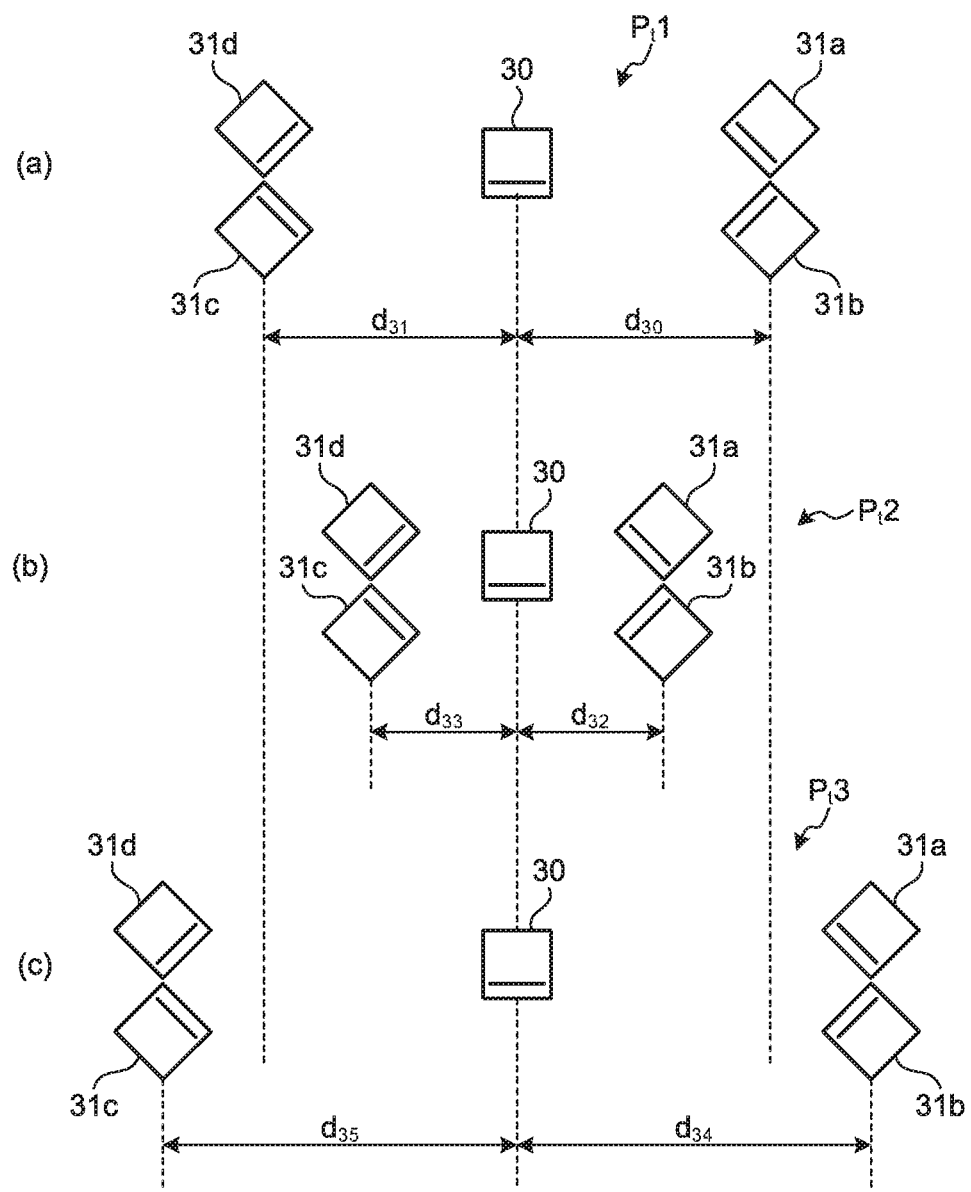
FIG. 13 is a diagram that illustrates the position correction by the antenna-position calculating unit in a capsule endoscope system according to a fourth embodiment.

FIG. 13 is a diagram that illustrates the position correction by the antenna-position calculating unit in the capsule endoscope system according to the fourth embodiment, and it is a diagram that illustrates multiple reference location patterns. According to the fourth embodiment, as illustrated in FIG. 13(a) to (c), three reference location patterns are previously set.

FIG. 13(a) illustrates a reference location pattern $P_r1$ that is similar to the subject having the normal body form. In the reference location pattern $P_r1$, the distance from the receiving antennas 31a, 31b to the reference antenna 30 is set to a distance $d_{30}$, and the distance from the receiving antennas 31c, 31d to the reference antenna 30 is set to a distance $d_{31}$ (=$d_{30}$).

FIG. 13(b) illustrates a reference location pattern $P_r2$ that is similar to the subject having a thin body form. In the reference location pattern $P_r2$, the distance from the receiving antennas 31a, 31b to the reference antenna 30 is set to a distance $d_{32}$ (<$d_{30}$), and the distance from the receiving antennas 31c, 31d to the reference antenna 30 is set to a distance $d_{33}$ (=$d_{32}$).

FIG. 13(c) illustrates a reference location pattern $P_r3$ that is similar to the subject having an overweight body form. In the reference location pattern $P_{r3}$, the distance from the receiving antennas 31a, 31b to the reference antenna 30 is set to a distance $d_{34}$ (>$d_{30}$), and the distance from the receiving antennas 31c, 31d to the reference antenna 30 is set to a distance $d_{35}$ (=$d_{34}$).

Figure 14:
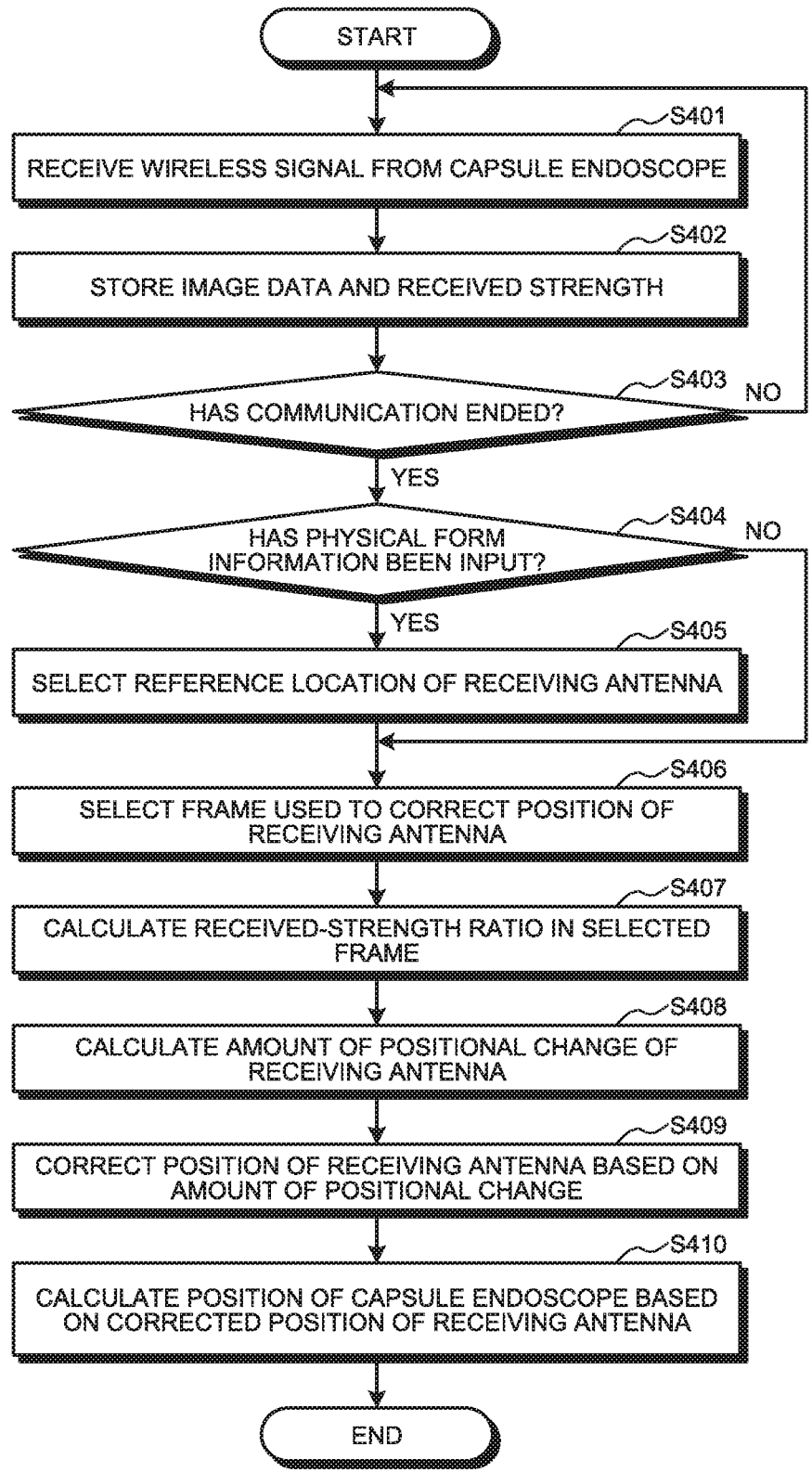
FIG. 14 is a flowchart that illustrates a position detection process performed by the receiving device in the capsule endoscope system according to the fourth embodiment.

Next, the process to detect the position of the capsule endoscope 2 as performed by the receiving device 4 is explained. FIG. 14 is a flowchart that illustrates the position detection process performed by the receiving device in the capsule endoscope system according to the fourth embodiment.

First, at Step S401, the receiving unit 401 receives a wireless signal from the capsule endoscope 2. The receiving unit 401 acquires the image data and the received strength from the wireless signal and stores the image data and the received strength in a related manner in the storage unit 407 (Step S402).

At Step S403 subsequent to Step S402, the control unit 408 determines whether the communication with the capsule endoscope 2 has ended. In the same manner as in the above-described first embodiment, when it is determined that the communication with the capsule endoscope 2 has not ended (Step S403: No), the control unit 408 returns to Step S401 to receive a new wireless signal. Conversely, when it is determined that the communication with the capsule endoscope 2 has ended (Step S403: Yes), the control unit 408 proceeds to Step S404.

At Step S404, the control unit 408 determines whether the physical form information on the subject has been input via the input unit 405. When it is determined that the physical form information has not been input (Step S404: No), the control unit 408 sets the usual reference location pattern (e.g., the normal-type reference location pattern $P_r1$) as the selected reference location pattern and proceeds to Step S406. Conversely, when it is determined that the physical form information has been input (Step S404: Yes), the control unit 408 proceeds to Step S405 to select the reference location pattern based on the physical form information. At Step S405, when for example "thin type" has been input as the physical form information, the control unit 408 selects the thin-type reference location pattern $P_r2$.

At Step S406 to S409 subsequent to Step S405, the antenna-position calculating unit 403 uses the reference location pattern selected based on the physical form information to calculate the position of the receiving antenna.

At Step S406, the antenna-position calculating unit 403 selects the frame having the received strength used to correct the position of the receiving antenna. In the same manner as in the first embodiment, the antenna-position calculating unit 403 selects the frame having the highest received strength with regard to the reference antenna 30 among the received strengths of the respective frames stored in the storage unit 407. The antenna-position calculating unit 403 sets the selected frame as the frame used to correct the positions of the receiving antennas 31a to 31d.

At Step S407 subsequent to Step S406, the antenna-position calculating unit 403 calculates the received-strength ratio in the selected frame. The antenna-position calculating unit 403 calculates, in the selected frame, the received-strength ratio of each of the receiving antennas with respect to the received strength of the reference antenna 30.

At Step S408 subsequent to Step S407, the antenna-position calculating unit 403 calculates the amount of positional change of each of the receiving antennas 31a to 31d from the reference location by using the received-strength ratio calculated at Step S407 and the correction function (see FIG. 4) stored in the antenna-information storage unit 407a.

At Step S409 subsequent to Step S408, the antenna-position calculating unit 403 corrects the positions of the receiving antennas 31a to 31d with respect to the reference location based on the amount of positional change calculated at Step S408. Specifically, with regard to the selected reference location pattern, the antenna-position calculating unit 403 moves the position of the receiving antenna corresponding to the reference location by the amount of positional change, thereby determining the position of the receiving antenna.

At Step S410 subsequent to Step S409, the capsule-position calculating unit 404 calculates the position of the capsule endoscope 2 in each frame based on the position of the reference antenna 30 and the positions of the receiving antennas 31a to 31d corrected at Step S409.

Afterward, for example, the processing device 5 may generate a position detection result indicating the trajectory of the capsule endoscope 2 by using the position of the capsule endoscope 2 in each frame calculated at Step S410 and cause the display device 6 to display the position detection result together with the image captured by the capsule endoscope 2.

According to the above-described fourth embodiment, the same advantage as that in the above-described first embodiment may be obtained and, as the reference location pattern is selected based on input physical form information, correction may be made based on the antenna location that is similar to the location of the receiving antenna that may be attached to the subject. As a result, the amount of positional change from the reference location may be small, and the position correction of the receiving antenna with further higher accuracy may be performed.

Moreover, according to the above-described fourth embodiment, a parameter for the correction function may be changed in accordance with the physical form information.

Fifth Embodiment

Next, a fifth embodiment is explained. A capsule endoscope system according to the fifth embodiment is the same as the above-described capsule endoscope system 1.

According to the fifth embodiment, multiple reference location patterns are stored in the antenna-information storage unit 407a, and the reference location pattern to be used is selected based on the input information about the type of antenna.

According to the fifth embodiment, for example, information about the size (large size, medium size, small size)

of a receiving antenna is input. If the reference location patterns $P_r1$ to $P_r3$ illustrated in FIG. 13 are stored, the control unit 408 selects the reference location pattern $P_r1$ when the size of the receiving antenna is a medium size, selects the reference location pattern $P_r2$ when the size of the receiving antenna is a small size, and selects the reference location pattern $P_r3$ when the size of the receiving antenna is a large size.

The position detection process according to the fifth embodiment is performed in the same flow as that in the above-described fourth embodiment (FIG. 14). Specifically, at Step S404, the control unit 408 determines whether the information about the type of receiving antenna has been input via the input unit 405. Then, at Step S405 to S409, the antenna-position calculating unit 403 corrects the position of the receiving antenna by using the reference location pattern selected based on the information about the type of receiving antenna, and the capsule-position calculating unit 404 calculates the position of the capsule endoscope 2 in each frame.

According to the above-described fifth embodiment, the same advantage as that in the above-described first embodiment may be obtained and, as the reference location pattern is selected based on the input information about the type of receiving antenna, correction may be made based on the antenna location that is similar to the location of the receiving antenna that may be attached to the subject. As a result, the amount of positional change from the reference location may be small, and the position correction of the receiving antenna with further higher accuracy may be performed.

Sixth Embodiment

Figure 15:
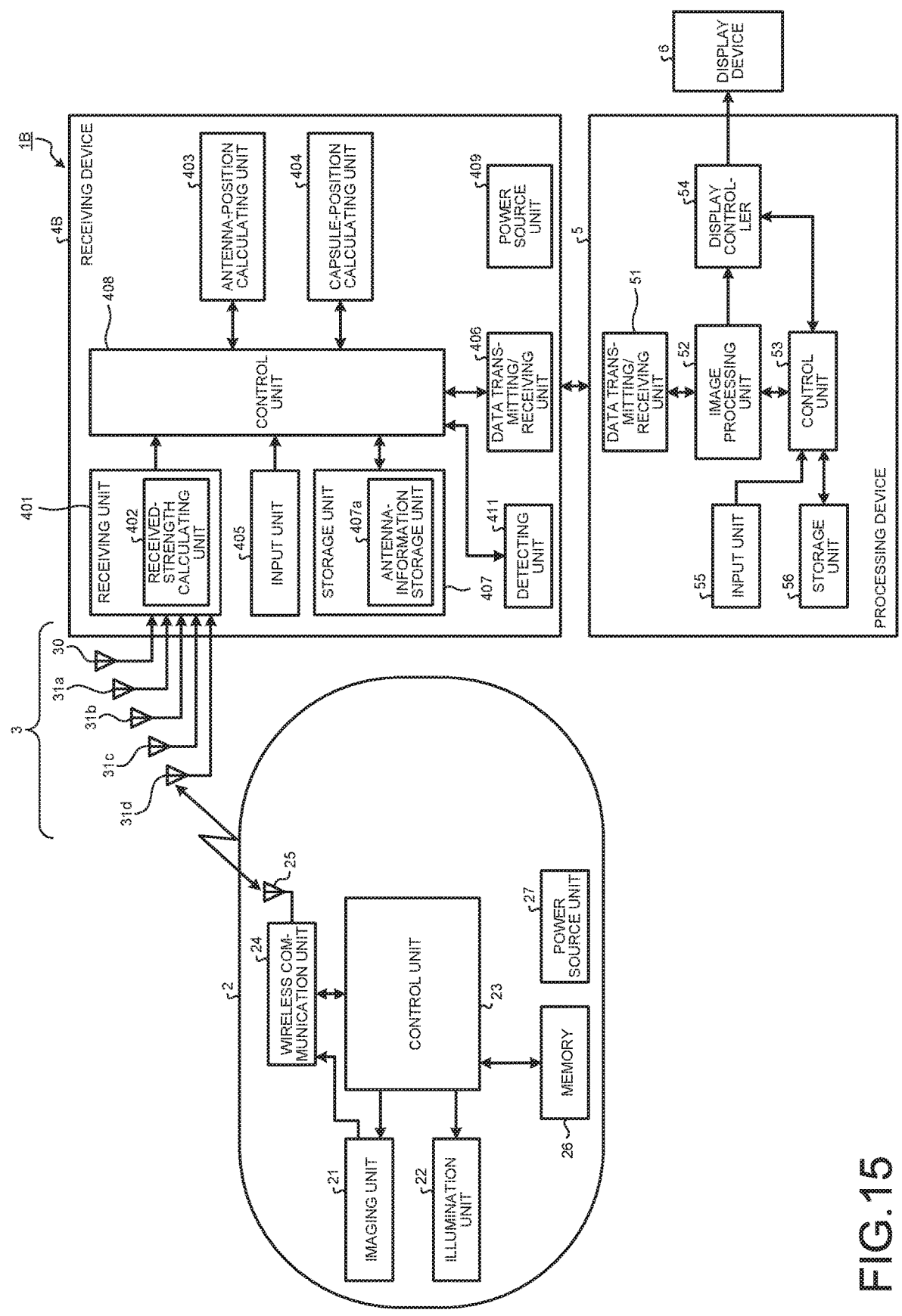
FIG. 15 is a block diagram that illustrates a schematic configuration of a capsule endoscope system according to a sixth embodiment.

Next, a sixth embodiment is explained. FIG. 15 is a block diagram that illustrates a schematic configuration of a capsule endoscope system according to the sixth embodiment.

A capsule endoscope system 1B according to the sixth embodiment includes: the capsule endoscope 2; the receiving device 4B that receives a wireless signal transmitted from the capsule endoscope 2 via the receiving antenna unit 3 including the receiving antennas (the reference antenna 30, the receiving antennas 31a to 31d) attached to the subject $H_1$ (or the subject $H_2$); and the processing device 5 that fetches an image signal, captured by the capsule endoscope 2, from the receiving device 4B via the cradle 5a, processes the image signal, and generates an image inside the subject $H_1$ (or the subject $H_2$). An image generated by the processing device 5 is displayed and output by, for example, the display device 6. According to the sixth embodiment, only the configuration of the receiving device 4B is different as compared with the configuration of the above-described capsule endoscope system 1.

The receiving device 4B further includes a detecting unit 411 as compared with the configuration of the above-described receiving device 4.

The detecting unit 411 detects the type of the receiving antenna unit 3 connected to the receiving device 4B. For example, the detecting unit 411 detects the type (e.g., the above-described size) of the receiving antenna unit 3 in accordance with the pattern of electrically connected pins among the pins provided in the connection part with the receiving antenna unit 3. The detecting unit 411 is configured by using a CPU, an ASIC, or the like.

Figure 16:
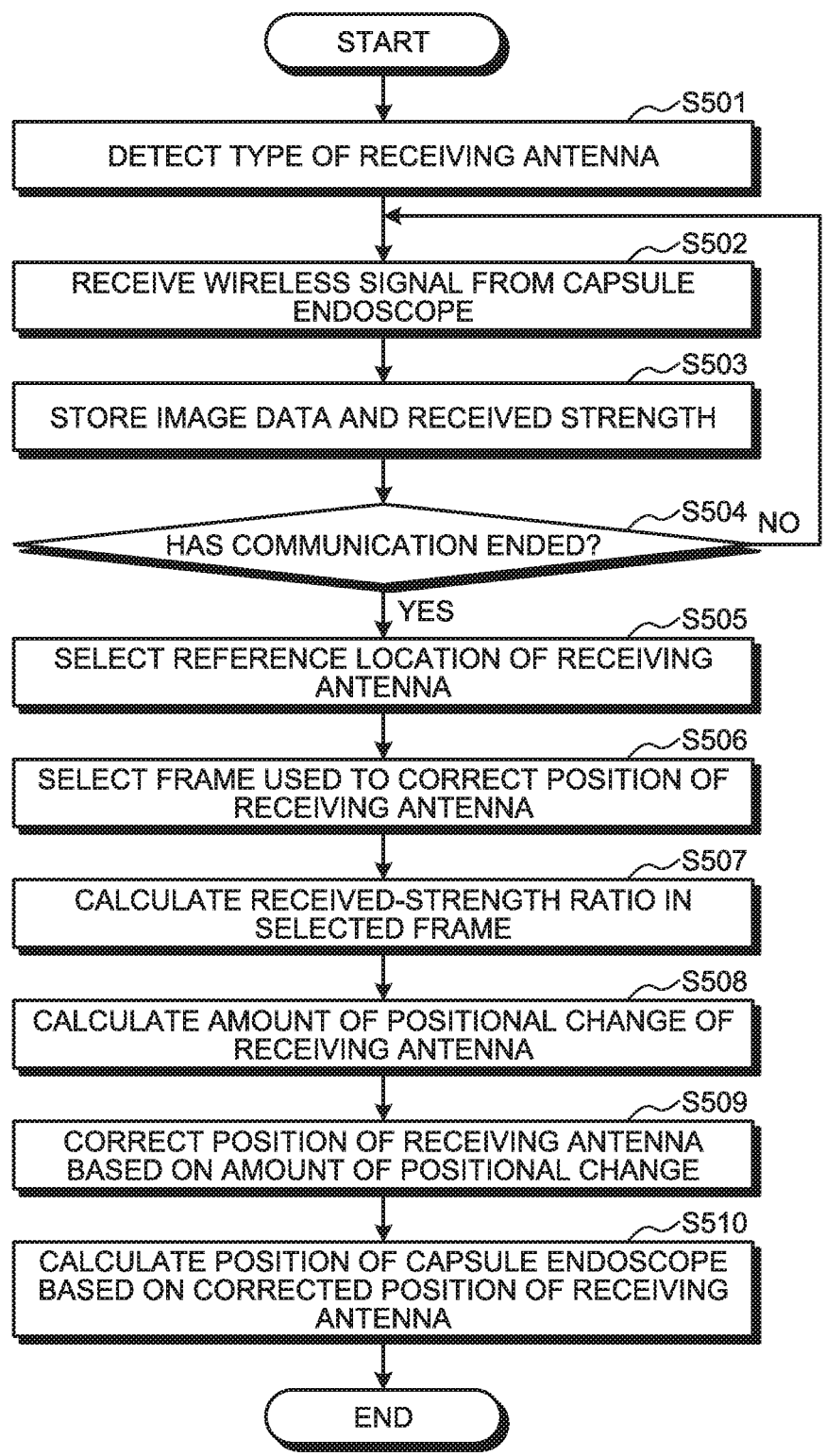
FIG. 16 is a flowchart that illustrates a position detection process performed by the receiving device in the capsule endoscope system according to the sixth embodiment.

Next, the process to detect the position of the capsule endoscope 2 as performed by the receiving device 4B is explained. FIG. 16 is a flowchart that illustrates the position detection process performed by the receiving device in the capsule endoscope system according to the sixth embodiment.

First, at Step S501, the detecting unit 411 detects the type of the connected receiving antenna unit 3. The detecting unit 411 generates detection information about the detected type. The detection information includes, for example, the above-described size of the receiving antenna.

Then, at Step S502, the receiving unit 401 receives a wireless signal from the capsule endoscope 2. The receiving unit 401 acquires the image data and the received strength from the wireless signal and stores the image data and the received strength in a related manner in the storage unit 407 (Step S503).

At Step S504 subsequent to Step S503, the control unit 408 determines whether the communication with the capsule endoscope 2 has ended. In the same manner as in the above-described first embodiment, when it is determined that the communication with the capsule endoscope 2 has not ended (Step S504: No), the control unit 408 returns to Step S502 to receive a new wireless signal. Conversely, when it is determined that the communication with the capsule endoscope 2 has ended (Step S504: Yes), the control unit 408 proceeds to Step S505.

At Step S505, the control unit 408 selects the reference location pattern based on the detection information generated by the detecting unit 411. For example, the control unit 408 selects the reference location pattern $P_r1$ when the size of the receiving antenna is a medium size, selects the reference location pattern $P_r2$ when the size of the receiving antenna is a small size, and selects the reference location pattern $P_r3$ when the size of the receiving antenna is a large size.

At Step S506 to S509 subsequent to Step S505, the antenna-position calculating unit 403 calculates the position of the receiving antenna by using the reference location pattern selected at Step S505.

At Step S506, the antenna-position calculating unit 403 selects the frame having the received strength used to correct the position of the receiving antenna. In the same manner as in the first embodiment, the antenna-position calculating unit 403 selects the frame having the highest received strength with regard to the reference antenna 30 among the received strengths of the respective frames stored in the storage unit 407. The antenna-position calculating unit 403 sets the selected frame as the frame used to correct the positions of the receiving antennas 31a to 31d.

At Step S507 subsequent to Step S506, the antenna-position calculating unit 403 calculates the received-strength ratio in the selected frame. The antenna-position calculating unit 403 calculates, in the selected frame, the received-strength ratio of each of the receiving antennas with respect to the received strength of the reference antenna 30.

At Step S508 subsequent to Step S507, the antenna-position calculating unit 403 calculates the amount of positional change of each of the receiving antennas 31a to 31d from the reference location by using the received-strength ratio calculated at Step S507 and the correction function (see FIG. 4) stored in the antenna-information storage unit 407a.

At Step S509 subsequent to Step S508, the antenna-position calculating unit 403 corrects the positions of the receiving antennas 31a to 31d with respect to the reference location based on the amount of positional change calculated at Step S508.

At Step S510 subsequent to Step S509, the capsule-position calculating unit 404 calculates the position of the capsule endoscope 2 in each frame based on the position of the reference antenna 30 and the positions of the receiving antennas 31a to 31d corrected at Step S509.

Afterward, for example, the processing device 5 may generate a position detection result indicating the trajectory of the capsule endoscope 2 by using the position of the capsule endoscope 2 in each frame calculated at Step S510 and cause the display device 6 to display the position detection result together with the image captured by the capsule endoscope 2.

According to the above-described sixth embodiment, the same advantage as that in the above-described first embodiment may be obtained and, as the reference location pattern is selected based on the information on the receiving antenna unit 3 detected by the detecting unit 411, correction may be made based on the antenna location that is similar to the location of the receiving antenna that may be attached to the subject. As a result, the amount of positional change from the reference location may be small, and the position correction of the receiving antenna with further higher accuracy may be performed.

Although the embodiments for carrying out the present disclosure are explained above, the present disclosure should not be limited to only the above-described embodiments and modifications. The present disclosure is not limited to the above-described embodiments and modifications, and it may include various embodiments without departing from the technical idea described in the scope of claims. Furthermore, the configurations in embodiments and modifications may be combined as appropriate.

In the explanation according to the above-described first to sixth embodiments, there are one reference antenna and multiple receiving antennas, and the positions of the receiving antennas are corrected; however, this is not a limitation, and there may be multiple reference antennas and one receiving antenna. The configuration having one reference antenna and one receiving antenna is also applicable.

Furthermore, an execution program for each process performed by each component in the capsule endoscope, the receiving device, and the processing device of the capsule endoscope system according to the first to sixth embodiments may be configured to be provided by being stored, in the form of a file that is installable and executable, in a recording medium readable by a computer, such as a CD-ROM, a flexible disk (FD), a CD-R, or a DVD, or may be configured to be provided by being stored in a computer connected to a network, such as the Internet, and downloaded via the network. Furthermore, it may be configured to be provided or distributed via a network such as the Internet.

As described above, the position detection apparatus, the position detection system, and the position detection method according to the present disclosure are advantageous in detecting the position of the capsule endoscope with high accuracy even when the relative position of the receiving antennas is changeable.

According to the present disclosure, there is an advantage such that it is possible to detect the position of the capsule endoscope with high accuracy even when the relative position of the receiving antennas is changeable.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detection apparatus comprising:
a first antenna attached to a predetermined position of a subject and configured to receive a wireless signal transmitted from a medical apparatus inserted into the subject;
a second antenna attached to the subject at a different position relative to the predetermined position of the subject to which the first antenna is attached, wherein the different position varies based on a physical form of the subject, and configured to receive the wireless signal; and
a processor comprising hardware, the processor being configured to:
calculate a first received strength of the wireless signal received by the first antenna and a second received strength of the wireless signal received by the second antenna;
calculate an attachment position of the second antenna based on the first received strength and the second received strength; and
calculate a position of the medical apparatus based on the attachment position of the second antenna calculated.
wherein the processor is configured to select, from a plurality of wireless signals sequentially received, the wireless signal for which the first received strength and the second received strength is calculated, and
wherein the processor is configured to, in calculating the attachment position:
calculate a ratio of the first received strength and the second received strength;
calculate, based on the ratio, an amount of positional change of the second antenna representing a difference between a possible attachment position of the second antenna and a previously stored reference location of the second antenna; and
calculate the attachment position of the second antenna based on the amount of positional change of the second antenna calculated.

2. The position detection apparatus according to claim 1, wherein the processor is configured to:
access a memory that stores a reference received strength of each antenna in a previously set reference location of the first and the second antennas,
select, from the plurality of wireless signals sequentially received, the wireless signal based on a difference between the reference received strength and the first and the second received strengths.

3. The position detection apparatus according to claim 1, wherein the processor is configured to select, from the plurality of wireless signals sequentially received, the wireless signal having the first received strength that is greater than a predetermined threshold.

4. The position detection apparatus according to claim 1, further comprising:
a third antenna, wherein the second antenna and the third antenna are attached to the subject at symmetric positions with respect to the first antenna, and
wherein the processor is configured to:
calculate a third received strength of the wireless signal received by the third antenna; and
select, from the plurality of wireless signals sequentially received, the wireless signal of which the second received strength and the third received strength are identical.

5. The position detection apparatus according to claim 1, wherein the processor is configured to:
- access a memory that stores a plurality of sets of reference locations of the first antenna and the second antenna;
- receive an input of information of the physical form of the subject and information about types of the first antenna and the second antenna; and
- select one of the plurality of sets of reference locations including the previously stored reference location of the second antenna based on the information of the physical form of the subject and the information about types of the first antenna and the second antenna.

6. The position detection apparatus according to claim 1, wherein the processor is configured to:
- access a memory that stores a plurality of sets of reference locations of the first antenna and the second antenna;
- detect types of the first antenna and the second antenna; and
- select one of the plurality of sets of reference locations including the previously stored reference location of the second antenna based on the types of the first antenna and the second antenna detected.

7. The position detection apparatus according to claim 1, wherein the processor is configured to:
- calculate a ratio of the second received strength to the first received strength;
- calculate an amount of positional change of the second antenna from a predetermined position based on the ratio and correction information, wherein the correction information is a correction function or a look-up table indicating a relation between the ratio of the second received strength to the first received strength and the amount of positional change of the second antenna; and
- calculate the attachment position of the second antenna based on the positional change of the second antenna calculated.

8. A position detection system comprising:
- a medical apparatus configured to be inserted into a subject and to transmit a wireless signal;
- a first antenna attached to a predetermined position of the subject and configured to receive the wireless signal;
- a second antenna attached to the subject at a different position relative to the predetermined position of the subject to which the first antenna is attached, wherein the different position varies based on a physical form of the subject, and configured to receive the wireless signal; and
- a processor comprising hardware, the processor being configured to:
  - calculate a first received strength of the wireless signal received by the first antenna and a second received strength of the wireless signal received by the second antenna;
  - calculate an attachment position of the second antenna based on the first received strength and the second received strength; and
  - calculate a position of the medical apparatus based on the attachment position of the second antenna calculated,
- wherein the processor is configured to select, from a plurality of wireless signals sequentially received, the wireless signal for which the first received strength and the second received strength is calculated, and
- wherein the processor is configured to, in calculating the attachment position:
  - calculate a ratio of the first received strength and the second received strength;
  - calculate, based on the ratio, an amount of positional change of the second antenna representing a difference between a possible attachment position of the second antenna and a previously stored reference location of the second antenna; and
  - calculate the attachment position of the second antenna based on the amount of positional change of the second antenna calculated.

9. A position detection method comprising:
- calculating, a first received strength of a wireless signal, transmitted from a medical apparatus inserted into a subject, received by a first antenna attached to a predetermined position of the subject and a second received strength of the wireless signal received by a second antenna attached to the subject at a different position relative to the predetermined position of the subject to which the first antenna is attached, wherein the first position varies based on a physical form of the subject;
- calculating an attachment position of the second antenna based on the first received strength and the second received strength; and
- calculating a position of the medical apparatus based on the attachment position of the second antenna calculated,
- wherein the position detection method further comprises selecting, from a plurality of wireless signals sequentially received, the wireless signal for which the first received strength and the second received strength is calculated, and
- wherein the calculating the attachment position comprises:
  - calculating a ratio of the first received strength and the second received strength;
  - calculating, based on the ratio, an amount of positional change of the second antenna representing a difference between a possible attachment position of the second antenna and a previously stored reference location of the second antenna; and
  - calculating the attachment position of the second antenna based on the amount of positional change of the second antenna calculated.

* * * * *